(12) United States Patent
Madduri et al.

(10) Patent No.: US 10,612,031 B2
(45) Date of Patent: Apr. 7, 2020

(54) EUKARYOTIC CELL-FREE PROTEIN EXPRESSION SYSTEM THAT DOES NOT REQUIRE AN ARTIFICIAL ENERGY REGENERATION SYSTEM

(71) Applicants: Dow AgroSciences LLC, Indianapolis, IN (US); Fraunhofer-Gesellschaft zur Förderung der angewandten Forschung e.V., München (DE)

(72) Inventors: Krishna Madduri, Carmel, IN (US); Janna Armstrong, Indianapolis, IN (US); Audrey Etter, Indianapolis, IN (US); Matthias Buntru, Aachen (DE); Simon Vogel, Aachen (DE); Stefan Schillberg, Aachen (DE); Rainer Fischer, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/893,346

(22) Filed: Feb. 9, 2018

(65) Prior Publication Data
US 2018/0245087 A1 Aug. 30, 2018

Related U.S. Application Data

(60) Provisional application No. 62/457,073, filed on Feb. 9, 2017.

(51) Int. Cl.
*C12N 15/67* (2006.01)
*C12P 21/02* (2006.01)

(52) U.S. Cl.
CPC ............ *C12N 15/67* (2013.01); *C12P 21/02* (2013.01)

(58) Field of Classification Search
CPC .................................................. C12P 21/02
See application file for complete search history.

(56) References Cited

U.S. PATENT DOCUMENTS

| | | | |
|---|---|---|---|
| 5,492,817 | A | 2/1996 | Thompson et al. |
| 5,593,856 | A | 1/1997 | Choi et al. |
| 5,665,563 | A | 9/1997 | Beckler |
| 7,338,789 | B2 | 3/2008 | Swartz et al. |
| 2008/0138857 | A1 | 6/2008 | Swartz et al. |
| 2009/0087879 | A1 | 4/2009 | Gerritis et al. |

FOREIGN PATENT DOCUMENTS

| WO | 2004016778 | 2/2004 |
|---|---|---|
| WO | 2015165583 | 11/2015 |
| WO | 2015193897 | 12/2015 |

OTHER PUBLICATIONS

Poyton et al. PNAS, 1975, 72(1):172-176.*
Harbers FEBS Letters, 2014, 588:2762-2773.*
Bard et al. PNAS 1985, 82:3983-3987.*
Walker et al. PNAS, 1976, 73(4):1126-1130.*
Kim et al., Regeneration of adenosine triphosphate from glycolytic intermediates for cell-free protein synthesis; Biotechnol Bioeng. Aug. 20, 2001; 74(4): 309-16.
Jewett et al., An integrated cell-free metabolic platform for protein production and synthetic biology; Mol. Syst Biol. 2008; 4: 220.
Brodel et al., Cell-free protein expression based on extracts from CHO cells; Biotechnol Bioeng Jan. 2014; 111(1): 25-36.
Ezure et al., Cell-free protein synthesis system prepared from insect cells by freeze-thawing; Biotechnol Prog. Nov.-Dec. 2006; 22(6): 1570-7.
Hodgman et al., Optimized extract preparation methods and reaction conditions for improved yeast cell-free protein synthesis; Biotechnol Bioeng. Oct. 2013; 110(10): 2643-54.
Schoborg et al., Substrate replenishment and byproduct removal improve yeast cell-free protein synthesis; Biotechnol J. May 2014; 9(5): 630-40.
Takai et al., The Wheat-Germ Cell-Free Expression System; Current Pharmaceutical Biotechnology; vol. 11, Issue 3, 2010; 272-278.
Buntru et al., Tobacco BY-2 cell-free lysate: an alternative and highly-productive plant-based in vitro translation system; BMC Biotechnology 2014, 14:37; http://www.biomedcentral.com/1472-6750-14-37; 11 pgs.
Buntru et al., A Cersatile Coupled Cell-Free Transcription-Translation System Based on Tobacco BY-2 Cell Lysates; 3iotechnology and Bioengineering, vol. 112, No. 5, May 2015; pp. 867-878.
Madin et al.; A highly efficient and robust cell-free protein synthesis system prepared from wheat ebryos: Plants apparently contain a suicide system directed at ribosomes; PNAS; Jan. 18, 2000; vol. 97, No. 2; pp. 559-564.
Takai, et al.; Practical cell-free protein synthesis system using purified wheat embryos; Nature Protocols; vol. 5, No. 2; 2010; pp. 227-238.
International Search Report and Written Opinion for PCT/US2018/017602, dated May 23, 2018.

\* cited by examiner

*Primary Examiner* — Bin Shen
(74) *Attorney, Agent, or Firm* — Magleby Cataxinos & Greenwood

(57) ABSTRACT

This disclosure concerns the systems, methods, and kits for the in vitro synthesis of biological macromolecules in a reaction utilizing cell lysates containing plastids, mitochondria and/or chloroplasts, wherein creatine phosphate and creatine kinase are not added to the reaction to provide artificial energy regeneration.

18 Claims, 14 Drawing Sheets

Specification includes a Sequence Listing.

EUKARYOTIC CELL-FREE PROTEIN EXPRESSION SYSTEM THAT DOES NOT REQUIRE AN ARTIFICIAL ENERGY REGENERATION SYSTEM

CROSS-REFERENCE TO RELATED APPLICATION

This application claims the benefit of priority from U.S. Provisional Patent Application Ser. No. 62/457,073, filed Feb. 9, 2017, the disclosure of which is hereby incorporated herein in its entirety by this reference.

FIELD OF THE DISCLOSURE

The present disclosure relates to the in vitro production of biopolymers. Some embodiments relate to the production of, for example, polypeptides, polynucleotides, and/or polysaccharides in a eukaryotic cell-free system. Particular embodiments utilize organelles (e.g., plastids, mitochondria or chloroplasts) to provide energy for the continued production of biopolymers in the cell-free system, which eliminates the need for certain undesirable energy-storing molecules in the system; e.g., creatine phosphate.

BACKGROUND

The increasing demand for new therapeutic proteins, technical enzymes, protein engineering, and functional genomics requires a rapid and efficient protein production and screening platform. Leader et al. (2008) Nat. Rev. Drug Discov. 7(1):21-39; Swartz (2012) Aiche J. 58(1):5-13. The emerging technology of cell-free protein synthesis (CFPS) can help to satisfy this demand. Carlson et al. (2012) Biotechnol. Adv. 30(5):1185-94. Compared to cell-based expression, CFPS offers advantages such as shorter process times and the direct control and monitoring of reaction conditions. Swartz (2012), supra. PCR products can be used directly for the simultaneous expression of multiple proteins without laborious cloning and transformation steps. Wu et al. (2007) Angew. Chem. Int. Ed. Engl. 46(18):3356-8; Yabuki et al. (2007) J. Struct. Funct. Genomics 8(4):173-91; Gan & Jewett (2014) Biotechnol. J. 9(5):641-51. CFPS platforms allow the addition of accessory factors that promote protein folding (Ozawa et al. (2005) J. Biomol. NMR 32(3):235-41; Endo et al. (2006) Mol. Biotechnol. 33(3):199-209; Matsuda et al. (2006) J. Struct. Funct. Genomics 7(2):93-100), or the incorporation of unnatural amino acids (Albayrak & Swartz (2013) Nucleic Acids Res. 41(11):5949-63; White et al. (2013) Methods 60:70-4). They also facilitate the expression of cytotoxic proteins that cannot be produced in living cells. Xu et al. (2005) Appl. Biochem. Biotechnol. 127(1):53-62; Schwarz et al. (2008) Proteomics 8(19):3933-46; Xun et al. (2009) Protein Expr. Purif. 68(1):22-7.

*Escherichia coli* cell-free lysates are widely used and are advantageous because of their low cost, scalability, and high productivity. Zawada et al. (2011) Biotechnol. Bioeng. 108(7):1570-8; Caschera & Noireaux (2014) Biochimie 99:162-8. However, because the lysates originate from bacteria, they are unsuitable for the production of complex proteins with multiple subdomains due to inefficient oxidative folding, and the absence of chaperones and glycosylation machinery. Eukaryotic cell-free systems are better suited for the expression of such proteins, and support most forms of post-translational modification. Chang et al. (2005) J. Mol. Biol. 353(2):397-409; Zhang & Kaufman (2006) Handb. Exp. Pharmacol. (172):69-91. The most frequently used systems are based on wheat germ extract (WGE), insect cell extract (ICE), and rabbit reticulocyte lysate (RLL). However, these systems are expensive, and extract preparation is complex. Carlson et al. (2012), supra. This has created a demand for additional eukaryotic CFPS, such as those based on *Leishmania tarentolae* (Mureev et al. (2009) Nat. Biotechnol. 27(8):747-52), Chinese hamster ovary (CHO) cells (Brodel et al. (2014) Biotechnol. Bioeng. 111(1):25-36), and *Saccharomyces cerevisiae* (Hodgman & Jewett (2013) Biotechnol. Bioeng. 110(10):2643-54; Gan & Jewett (2014), supra).

The use of cell-free systems to perform in vitro protein synthesis has been limited, for example, by the short reaction times and low protein production rates that are characteristic of such systems. These qualities lead to poor protein yields and excessive costs per unit of protein produced.

Longer reaction times are obtainable through the use of a continuous translation reaction, using a continuous flow system. Spirin et al. (1988) Science 242:1162-1164. Continuous reactions are performed over tens (or even hundreds) of hours, and methods relying on continuous flow must constantly supply necessary reaction substrates to the chamber. Thus, these reactions require a substantial investment of time and resources. Furthermore, translation in a "continuous" system is directed towards producing large amounts of protein, and the system differs substantially from those used to perform static ("batch") in vitro translation reactions. Static reactions can be run in a small reaction volume (e.g., microliters), and are not directed towards producing preparative amounts (e.g., milligrams) of proteins. Such batch reactions may be completed in one to two hours. For all of the foregoing reasons, while it increases the reaction duration and protein yield as compared to a corresponding batch system, a continuous reaction system requires more expensive reagents.

BRIEF SUMMARY OF THE DISCLOSURE

A general strategy disclosed herein utilizes organelles in a cell-free lysate-based reaction to provide energy regeneration in the reaction system. This strategy is useful in some examples to accomplish the improved in vitro synthesis of biopolymers (e.g., polynucleotides, polypeptides, polysaccharides, and complex carbohydrates). In particular embodiments, the presence of mitochondria in a eukaryotic cell-free system results in an improved reaction system over conventional batch and continuous reactions, for example, by significantly reducing or eliminating the need for added energy-delivering reagents (e.g., creatine phosphate and/or creatine kinase), and/or amino acid supplementation, while also lengthening the reaction duration. In some examples, the disclosed cell-free polymerization reaction is significantly more efficient than conventional reactions currently utilized in the art.

Described herein are methods for synthesis of a biopolymer that comprise combining a cellular lysate comprising an organelle (e.g., plastids, chloroplasts and/or mitochondria), a polymer template, and monomeric units of the polymer in a reaction volume. In some embodiments, the reaction volume does not comprise the creatine phosphate/creatine kinase energy regeneration system, for example, so that no phosphate or minimal phosphate is added to the reaction volume. In particular embodiments, the organelle is a mitochondrion. In some embodiments, the cellular lysate is a eukaryotic cell lysate; for example, a lysate from a plant (e.g., tobacco, corn, and soybean) cell. A cellular lysate in some examples is a lysate from Bright Yellow-2 (BY-2) tobacco cells. In some embodiments, the polymer template is a DNA molecule or an RNA molecule. Reactions utilizing RNA as the polymer template produce polypeptides as the biopolymer from monomeric amino acids through a translation reaction. Reactions utilizing DNA as the polymer template may be utilized to produce further nucleic acid molecules (e.g., DNA and RNA) as a biopolymer from monomeric nucleotides through an in vitro replication or transcription reaction, or to produce polypeptides through a translation reaction that is coupled to transcription from the template. In certain embodiments, a method for energy-free synthesis of a biopolymer may comprise, for example and without limitation, adding the organelle(s), the polymer template, and/or monomeric units to the reaction volume, and/or isolating the biopolymer from the reaction volume. In some examples, the reaction volume does not require amino acid supplementation to support protein expression, as lysate components are capable of generating amino acids using endogenous biosynthesis pathways starting with intermediates from the TCA cycle. In some such examples, therefore, the amino acids present in the lysate comprising the organelle(s) may be sufficient to support extended synthesis of polypeptides.

The disclosed cellular lysate systems may be supplemented with only a minimal amount of exogenous creatine phosphate, a minimal amount of creatine kinase or both, so long as the reaction volume comprises exogenous creatine phosphate and/or creatine kinase in amounts considered unsuitable for an energy regeneration system. For example, a reaction volume may contain no more than 15 mM, no more than 10 mM, no more than 5 mM, no more than 1 mM, no more than 500 µM, no more than 100 µM, no more than 50 µM, or no more than 10 µM added creatine phosphate. In another example, a reaction volume may contain no more than 100 µg/mL, no more than 50 µg/mL, no more than 10 µg/mL, no more than 5 µg/mL, no more than 1 µg/mL, than 0.5 µg/mL, or no more than 0.1 µg/mL added creatine kinase. These amounts are unsuitable for, and thus require the inclusion of cellular organelle such as plastids, mitochondria or chloroplasts in accordance with the methods and systems disclosed herein, to sustain biopolymer synthesis (including to sustain biopolymer synthesis for the prolonged periods disclosed herein).

Some embodiments include systems for synthesis of a biopolymer without using an artificial energy regeneration system. In these embodiments, the system comprises an aqueous cellular lysate, a (endogenous or heterologous) cellular organelle, a polymer template. In particular embodiments, the system also includes monomeric units of the polymer. Conventional cell-free systems for in vitro biopolymer synthesis further comprise creatine phosphate and creatine kinase, which is used for energy regeneration in the system as the synthesis reaction proceeds. In embodiments herein, the system is substantially devoid of creatine phosphate; no creatine phosphate and creatine kinase is added to the system. In certain examples, the system comprises no creatine phosphate or creatine kinase. In particular embodiments, a system for synthesis of a biopolymer may further comprise, for example and without limitation, a pH buffer, magnesium (e.g., $Mg(C_5H_8NO_4)_2$), potassium (e.g., $KC_5H_8NO_4$), nucleosides (e.g., nucleoside triphosphates, nucleoside diphosphates, and nucleoside monophosphates), enzymes (e.g., RNA polymerase), and chloramphenicol. In specific embodiments, no amino acids other than glutamate salt(s) are added to those already present in the system (i.e., the amino acids present in the lysate and organelle). In some examples, a system according to the foregoing may show a prolonged activity of greater than 20 hours (e.g., about 40 hours), and may produce significantly more (e.g., about 60% more) target protein than an otherwise identical conventional system comprising added creatine phosphate and creatine kinase.

Some embodiments include a kit for synthesis of a biopolymer without using an artificial energy regeneration system. In some embodiments, a kit comprises components of a system for synthesis of a biopolymer without using an artificial energy regeneration system, and written instructions for directing the use of the kit. For example and without limitation, a kit may comprise one or more of: an aqueous cellular lysate, a (endogenous or heterologous) cellular organelle, a polymer template, and monomeric units of the polymer, disposed in one or more separate volumes, together with instructions specifying the admixture of the kit components and any exogenous components without creatine phosphate and creatine kinase. By way of further example, a kit may further comprise one or more of a pH buffer, magnesium, potassium, nucleosides, enzymes (e.g., RNA polymerase), and chloramphenicol. A kit for synthesis of a biopolymer according to specific embodiments may comprise an aqueous cellular lysate (e.g., comprising chloroplasts and/or mitochondria), monomeric units of a polymer (e.g., nucleosides), and written instructions. In such specific embodiments, the written instructions may direct a user to combine these components with a polymer template of interest (e.g., a DNA molecule encoding a polypeptide) and any other reagents, without adding creatine phosphate (with creatine kinase for energy regeneration) to the combination.

Embodiments herein incorporate active mitochondria for energy regeneration in an ongoing synthesis reaction, and thereby may be utilized to quantitatively investigate compounds or proteins affecting mitochondrial function within the context of in vitro synthesis. Furthermore, intermediates of the TCA cycle may be utilized during the synthesis reaction to produce amino acids, such that amino acid supplementation is not required for prolonged polypeptide synthesis. In some embodiments, a cellular lysate for use in the methods, systems, and kits herein comprises chloroplasts, which reduces oxygen-dependency of the synthesis reaction. For example, a cellular lysate may be prepared from photosynthetic active cells, such that plastids, chloroplasts and/or mitochondria are retained in the lysate, while undesirable cellular material is removed. In such specific examples, the methods, systems, and kits herein may utilize plastid-derived energy, mitochondrion-derived energy regeneration, chloroplast-derived energy regeneration, or a combination of both.

The foregoing and other features will become more apparent from the following detailed description of several embodiments, which proceeds with reference to the accompanying figures.

BRIEF DESCRIPTION OF THE FIGURES

FIG. 1(A) shows a comparison of the system's performance with a system that includes creatine phosphate (CP) and creatine kinase (CK). Coupled transcription-translation reactions were carried out using a reporter gene (i.e., eYFP) as a template at 25° C. for 52 hours. The yield of the fluorescent reporter protein was determined by measuring the fluorescence intensity using a fluorescence reader with 485/20 nm excitation and 528/20 nm emission filters.). FIG. 1(B) shows the effect on reporter yield of the inhibition of the electron transport chain inhibition by sodium azide (Azide) and thenoyltrifluoroacetone (TTA), respectively. Means and standard deviations were calculated from three independent transcription-translation experiments.

FIG. 3(A) includes the impact of different concentrations of chloramphenicol on microbial growth (CFU/µL). FIG. 3(B) includes the impact of different antimicrobial substances on eYFP yield, normalized to the yield in a standard reaction without an antimicrobial substance (100%). FIG. 3(C) includes the impact of different antimicrobial substances on microbial growth (CFU/µL). FIG. 3(D) includes the impact of different concentrations of chloramphenicol on eYFP yield (µg/mL).

DETAILED DESCRIPTION

I. Overview of Several Embodiments

Figure 1A:
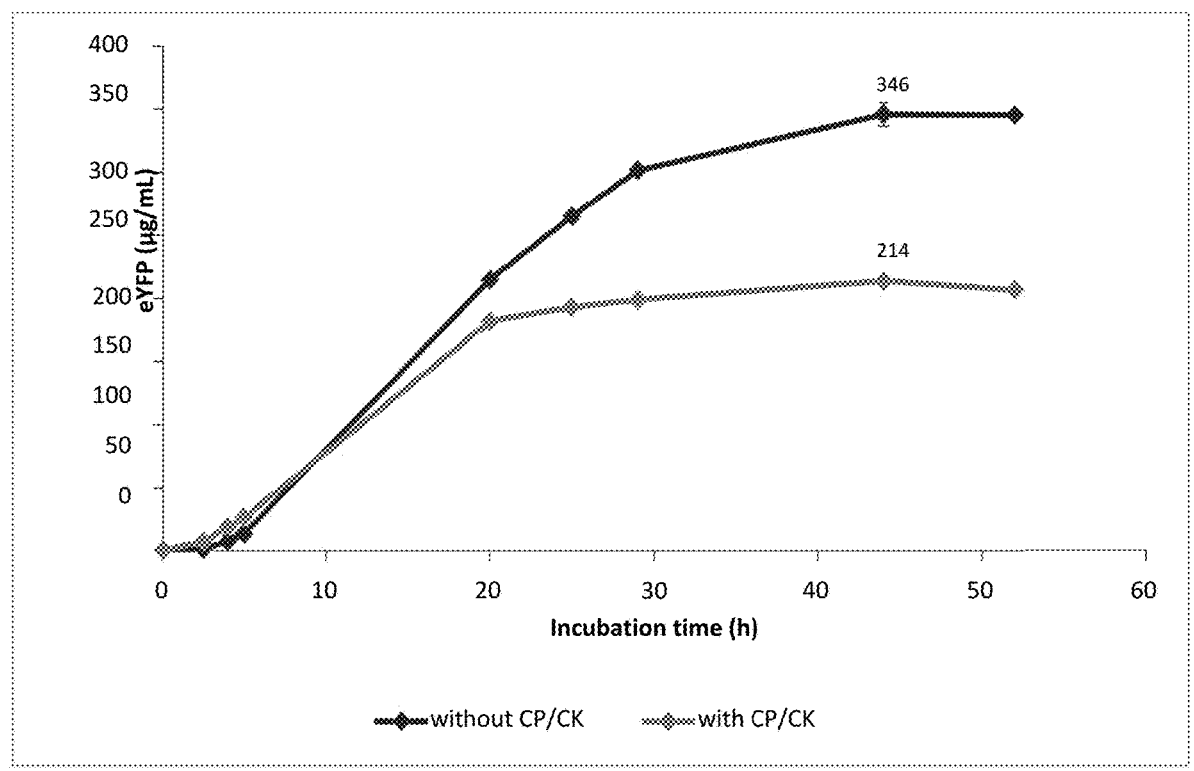
FIGS. 1A and 1B includes the elements and performance of a system for synthesis of a biopolymer without artificial energy regeneration, including a tobacco BY-2 cellular lysate (BYL).

Cell-free protein synthesis (CFPS) systems based on crude lysates provide several advantages over in vivo systems, and are useful in a broad range of applications, including, inter alia, protein engineering, bio-pharmaceutical production, and research. Conventional crude lysates contain necessary components for translation, protein folding, and energy metabolism, so almost any protein encoded by a RNA template to be synthesized therein in the presence of amino acids, nucleotides, and salts, provided that the lysate is supplemented with energy-storing reagents. In coupled transcription/translation systems, an RNA polymerase can be added to direct the synthesis of a protein from a DNA template. In contrast to cellular synthesis, CFPS may allow shorter process times, reduced protein hydrolysis, and the ability to express toxic proteins or proteins containing specific chemical groups or unnatural amino acids at defined positions. Furthermore, the reaction may be controlled and monitored directly.

Disclosed herein is a cell-free system for biopolymer synthesis (e.g., polypeptide synthesis) that utilizes a cell lysate without an artificial energy regeneration system, eliminating the need for additional energy-storing reagents. In embodiments, the system utilizes a eukaryotic cell lysate comprising organelles (e.g., plastids, mitochondria or chloroplasts) for energy regeneration during the synthesis reaction by oxidative phosphorylation. In certain examples, the cell lysate is a tobacco BY-2 lysate including mitochondria derived from the BY-2 cells. In cellular eukaryotic systems during oxidative phosphorylation, electrons are transferred from electron donors to electron acceptors like oxygen via an electron transport chain located within the inner membrane of the mitochondria. These redox reactions release energy, which is used to phosphorylate ADP to ATP. Embodiments herein utilize the energy from this process to drive the continued synthesis of biopolymers in the lysate. Thus, in embodiments herein, inhibitors of the electron transport chain and airtight conditions may be used to stop the energy regeneration by oxidative phosphorylation, and thereby stop the synthesis reaction by ending the translational activity of the system. In some embodiments, the system includes plastids, chloroplasts, which may allow the reaction to proceed in anaerobic or substantially anaerobic conditions.

Conventional eukaryotic cell-free systems (e.g., wheat germ extract, and insect cell extract) lack mitochondria. Instead, these systems require the addition of creatine phosphate and creatine kinase to accomplish the necessary ATP regeneration to support protein expression. The large accumulation of free phosphate (derived from the creatine phosphate) that is added to the reaction mixture for energy regeneration in order to support protein expression is a significant limiting factor in the performance of these systems. Ezure et al. (2006) Biotechnol. Prog. 22(6):1570-7; Takai et al. (2010) Curr. Pharm. Biotechnol. 11:272-8; Brödel et al. (2014) Biotechnol. Bioeng. 111(1):25-36; Hodgman & Jewett (2013), supra; Schoborg et al. (2014) Biotechnol. J. 9(5):630-40. The free phosphate introduced into the system binds magnesium (which is needed for transcription and translation), resulting in an early breakdown of the synthetic performance and low product yields.

In order to prolong the synthetic performance, currently available eukaryotic cell-free systems use "continuous flow" reactions in dialysis mode to provide a long-lasting energy supply and to dilute inhibitory components like phosphate in the reaction compartment. Systems without an artificial energy regeneration system for biopolymer synthesis described herein reduce or eliminate the need for reaction dialysis, as they produce less inhibitory components, and have their own energy regenerative capacity. However, the systems herein may be utilized in a continuous flow configuration if desired, according to the discretion of the practitioner.

Compared to conventional eukaryotic cell-free protein expression systems, the systems for biopolymer synthesis described herein are in general cheaper, and they produce protein longer, resulting in increased biopolymer yield. Furthermore, the systems herein offer the possibility to investigate compounds or pathways affecting mitochondrial and/or chloroplast function, for example, as further enhancers of cell-free protein expression. Thus, the fundamentally different systems of embodiments herein may be optimized to provide even further benefits.

Some systems for biopolymer synthesis described herein are capable of supporting growth of microorganisms, and such growth may result in depletion of substrates in an IVTT reaction and/or protein degradation, resulting in reduced yield of a target protein. Therefore, in some embodiments, the system includes chloramphenicol to inhibit microbial growth, which may improve protein expression in these embodiments. In particular embodiments, the system includes chloramphenicol in an amount between, for example, 10-500 µg/mL (e.g., between 25-250 µg/mL, between 50-200 µg/mL, and between 100-200 µg/mL).

Described herein is the discovery that particular amounts of NTPs in a coupled in vitro transcription/translation (IVTT) reaction may provide surprisingly robust expression in some embodiments, which may be about 20% or more (e.g., 18% or more, 19% or more, 20% or more, 21% or more, 22% or more, 23% or more, 24% or more, 25% or more, between 18-25% more, between 19-23% more, and approximately 20% more) of what was expected from standard NTP amounts. Therefore, in some examples, the system may include approximately 150 mM ATP, approximately 40 mM GTP, approximately 20 mM CTP, and approximately 20 mM UTP. A further advantage of utilizing these reduced amounts of NTPs is reduced expense, as the amount of GTP (the most expensive NTP) is reduced from that of a conventional plant cell system.

Also described herein is the surprising discovery that several modifications of the systems herein may give substantial improvement in product yield and/or quality. For example, use of sorbitol during the protoplastation and evacuolation steps of lysate preparation may result in increased protein production while simultaneously further reducing the system cost, as sorbitol is cheaper than other commonly used osmolarity agents such as mannitol. By way of further example, increasing the proportion of lysate to 50-90% (e.g., 55-85%) (v/v) of an IVTT reaction leads to higher expression of several target proteins. Therefore, particular examples herein include use of a cell lysate, which has been prepared with sorbitol during protoplastation and evacuolation, for example, in an amount of about 60% by volume (e.g., 58%, 59%, 60%, 61%, and 62%), or about 80% (e.g., 78%, 89%, 80%, 81%, and 82%) by volume. By way of yet another example, the addition of glucosylglycerol dramatically increases the protein yield of an IVTT reaction. For example, glucosylglycerol in amounts between 0.25% and 4% resulted in up to 80% more protein, as compared to standard reactions without glucosylglycerol. Without being bound to any particular theory, glucosylglycerol improves reaction yield presumably by increasing protein and membrane stability. Therefore, in some embodiments, the system includes 0.25-4% (e.g., 0.25-2%, 0.25-1%, about 0.5%, and 1.5%) glucosylglycerol. By way of further example, even though it is not required, the addition of branched amino acids (BCAAs) BCAAs can be utilized to increase protein production. Therefore, in some embodiments, the system includes BCAAs in amounts between about 0.25-4 mM or in amounts from 0.5-2 mM (e.g., 0.48-2.2 mM, 0.5-2.0 mM, 0.5-1 mM, and about 1 mM).

According to the foregoing modifications, in specific embodiments herein, the production of a target protein in a coupled IVTT reaction may be extended for up to 64 hours. In one example, reactions with 80% lysate and 0.5% glucosylglycerol by volume yield almost 2.5 mg/mL eYFP.

II. Abbreviations

AAD-12 aryloxyalkanoate dioxygenase-12
ADP adenosine diphosphate
ATP adenosine triphosphate
BCAA branched chain amino acid
BY-2 Bright Yellow-2
BYL BY-2 cellular lysate
CFPS cell-free protein synthesis
CFU colony forming unit
CHO Chinese hamster ovary
CL cellulase enzyme
CK creatine kinase
CP creatine phosphate
Cry1F *Bacillus thuringiensis* Cry1F delta-endotoxin
Cry3A *B. thuringiensis* Cry3A delta-endotoxin
CTP cytidine triphosphate
DMSO dimethyl sulfoxide
DOE design of experiment
DTT dithiothreitol
EDTA ethylenediaminetetraacetic acid
eYFP enhanced yellow fluorescent protein
FADH flavin adenine dinucleotide
GTP guanosine triphosphate
ICE insect cell extract
IMAC immobilized metal-affinity chromatography
IVTT in vitro transcription and translation
NADH nicotinamide adenine dinucleotide
NADPH nicotinamide adenine dinucleotide phosphate
NEB New England Biolabs
NTP nucleoside triphosphate
PCR polymerase chain reaction
PEG polyethylene glycol
RLL rabbit reticulocyte lysate
SEC size-exclusion chromatography
TCA cycle tricarboxylic acid cycle ("Krebs cycle")
TTA thenoyltrifluoroacetone
UTP uridine triphosphate
UTR untranslated region
WGE wheat germ extract III. Terms Isolated: An "isolated" biological component (such as a nucleic acid or protein) has been substantially separated, produced apart from, or purified away from other biological components in the cell of the organism in which the component naturally occurs (i.e., other chromosomal and extra-chromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A nucleic acid molecule can include either or both naturally occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidates, and carbamates; charged linkages: for example, phosphorothioates, and phosphorodithioates; pendent moieties: for example, peptides; intercalators: for example, acridine, and psoralen; chelators; alkylators; and modified linkages: for example, and alpha anomeric nucleic acids). The term "nucleic acid molecule" also includes any topological conformation, including single-stranded, double-stranded, partially duplexed, triplexed, hairpinned, circular, and padlocked conformations.

Exogenous: The term "exogenous," as applied to components (e.g., plastids, mitochondria or chloroplasts) added to cellular lysate herein, refers to such components having a different origin than the cell lysate. For example, plastids, mitochondria or chloroplasts, which do not originate from the cellular lysate and which are added to the lysate, are exogenous to the cellular lysate. The term exogenous, may be applied to cell organelles such as plastids, mitochondria or chloroplasts from the same cell type or from a different cell type (e.g., cell from a different tissue or different species) as the cell type used to derive the cellular lysate, so long as in either case the organelles are not derived from the cellular lysate itself. Additionally, the term exogenous may be used herein to refer to components of an energy regeneration system (e.g., creatine phosphate and creatine kinase) that are added separately or in addition to any plastid, mitochondria or chloroplast organelles used in the cell lysate of a system disclosed herein.

IV. Systems for Biopolymer Synthesis

This disclosure provides systems for synthesis of a biopolymer without using an artificial regeneration system. Systems herein include compositions and methods that accomplish the enhanced in vitro synthesis of biopolymers, in which oxidative phosphorylation is activated, providing for increased yields in the absence of energy-storing reagents. Improved yield is obtained by a combination of reaction IVTT components, which may be assembled and mixed by the practitioner, or which may be provided to the practitioner in a kit as premixed components, unmixed components, or a combination of the two. The practitioner may utilize some or all of the components of a kit in combination with components provided by herself; for example, in some embodiments, a kit includes all the components of a system for protein synthesis other than a DNA or RNA template, which is provided by the practitioner to synthesize a protein of her choosing. Once all the components of the system are mixed in a reaction volume under appropriate environmental conditions, the reaction commences, and proceeds generally according to conventional in vitro cell-free synthesis reactions, with important changes described herein. The reaction may be allowed to proceed until one or more of the components (e.g., NTPs and amino acids) are exhausted in the reaction volume, or until it is halted by adjusting the environmental conditions to end the energy regeneration process in the system.

The methods and compositions disclosed herein mimic the cytoplasmic environment of a eukaryotic cell, and result in significant improvements in protein production and protein folding over the methods of the prior art. For example, because oxidative phosphorylation is active in the reaction volume, due to the presence of cellular organelles, the systems herein reduce or completely avoid the necessity of secondary energy sources that are associated with synthesis inhibition.

Systems of embodiments herein are useful for the production/replication of biopolymers, including, for example, amplification of DNA, transcription of RNA from DNA or RNA templates, translation of RNA into polypeptides, and the synthesis of complex carbohydrates from simple sugars. Enhanced synthesis includes in some examples one or more of: increases in the total or relative amount of biopolymer synthesized in the system; increases in the total or relative amount of biopolymer synthesized per unit of time; increases in the total or relative amount of biologically active biopolymer (e.g., properly folded and/or post-translationally modified protein) synthesized; increases in the total or relative amount of soluble biopolymer synthesized, and reduced expense in time and/or money required to synthesize a given amount of biopolymer.

Particular embodiments herein accomplish the translation of mRNA to produce polypeptides, which translation may be coupled to in vitro synthesis of mRNA from a DNA template. Such a cell-free system contains all the factors required for the translation of mRNA, for example, ribosomes, amino acids, tRNAs, aminoacyl synthetases, elongation factors, initiation factors, and ribosome recycling factors. In examples herein, such a cell-free system comprises a cell lysate prepared in the manner described herein from a eukaryotic cell, for example, a plant cell (e.g., a tobacco BY-2 cell).

Cell Lysate

Embodiments herein may be adapted to utilize any eukaryotic cellular lysate. Eukaryotic cell-free lysates retain a variety of post-translational processing activities. Eukaryotic cellular lysates also support the translation in vitro of a wide variety of viral and other prokaryotic RNAs, as well as eukaryotic mRNAs. Template mRNAs that have a codon usage that deviates from that of the organism from which the cell lysate is derived may be used efficiently, for example, by supplementing the system with rare tRNAs and/or amino acids in the organism. Particular examples herein utilize tobacco BY-2 cell lysates, which are shown to offer simple and cost-effective fermentation in suspension culture in both batch-culture and stirred-tank fermenters, and which are amenable to well-established genetic modification tools.

Preparation of a cell lysate according to embodiments herein may include, inter alia, disruption/removal of cell walls (for plant cells) and cell membranes, removal of lytic vacuoles, and removal of endogenous mRNAs.

Cell walls and membranes may be disrupted in some embodiments by techniques including, for example and without limitation, mechanical disruption, liquid homogenization, enzymatic digestion, high frequency sound waves, decompression, freeze/thaw cycles, and manual grinding. In particular embodiments herein, plant cell lysates are prepared by digesting the cell wall using one or more cell-wall digesting enzymes (e.g., Cellulase Onozuka RS™, Pectolyase Y-23™, Macerozyme R-10), and liquid enzymes (e.g., Rohament CL™, Rohament PL™, and Rohapect UF™, which were originally intended for the production of fruit juice and extracts). Rohament CL™ comprises a cellulase concentrate, Rohament PL™ is a pectinase concentrate, and Rohapect UF™ contains an enzyme complex including specialized pectinases and arabanases. The use of these enzyme combinations reduced the costs of protoplastation more than 100-fold, as compared to conventional methods.

Also during the lysate preparation, any lytic vacuoles may be removed. Such vacuoles contain undesirable enzymes, including proteases and ribonucleases, which interfere with the synthesis of polypeptides and mRNAs. In some embodiments herein, lytic vacuoles are removed by centrifugation in a Percoll gradient, or any other density gradient. Vacuoles have a low density, and thus can be separated from protoplasts, yielding high-density evacuolated protoplasts. In some examples, a stepwise Sucrose density gradient may be utilized for evacuolation, where the protoplasts are applied directly onto the Percoll-free top layer. After centrifugation, the evacuolated protoplasts will be separated from the vacuoles, for example, concentrated at the interface between the 40% and 70% Percoll layers (depending on the gradients used), whereas the separated, lower-density vacuoles will be in a lower-density gradient; for example, floating on the top layer.

Evacuolated protoplasts may then be washed and then disrupted by a Dounce tissue grinder or nitrogen decompression to protect labile cell components from oxidation. After the removal of nuclei and non-disrupted cells, the lysate may be treated to destroy endogenous mRNAs while leaving the integrity of the 18S and 28S ribosomal RNAs mainly unaffected, thereby minimizing background translation. In particular examples herein, nuclease S7 is used.

Template

To direct the synthesis of a biopolymer in the systems herein, a template must be present in the reaction, as stored information to be converted into the polymer. The template for cell-free protein synthesis can be either mRNA or DNA, encoding for any polynucleotide (DNA) or polypeptide (DNA and/or mRNA) of interest. A coupled transcription/translation system continuously generates mRNA from a DNA template with a recognizable promoter. Either the endogenous RNA polymerase may be used, or an exogenous RNA polymerase (e.g., a phage RNA polymerase, typically T7 or SP6), may be added directly to the reaction mixture. Alternatively, mRNA may be continually amplified by inserting the message into a template for QB replicase, an RNA-dependent RNA polymerase. In some embodiments, a vector containing a poly-A sequence at one end of the multiple cloning region is used as a template in an IVTT reaction. For example, such a vector may contain an SP6, T7, or T3 RNA polymerase promoter at the opposite end of the multiple cloning region, so that cloning into the vector produces a gene that is flanked by an RNA polymerase promoter at the 5' end and a poly-A sequence at the 3' end. In embodiments wherein mRNA is utilized as the template, the purified mRNA may be stabilized by chemical modification before it is added to the reaction mixture.

The nucleotide sequence of a DNA or mRNA sequence utilized as a template according to embodiments herein may be optimized to achieve higher levels of expression. Several mRNA structural characteristics affect translation efficiency, including untranslated regions (UTRs) at the 5' and 3' ends of the coding sequence. The structure of the 5' UTR influences translational initiation, termination, and mRNA stability. One of the rate-limiting steps in translational initiation is the binding of the mRNA to the 43S pre-initiation complex. The translational machinery is recruited by the 5'-cap, or translational enhancers in the leader sequence. In certain embodiments herein, a template mRNA may contain an untranslated region selected from a group comprising the 5' UTR in pCITE2a (which contains an internal ribosomal entry site (IRES) derived from Encephalomyocarditis virus (EMCV)); sequences from Barley yellow dwarf virus (BYDV) in vector pF3A; the 5' UTR from a baculovirus polyhedrin gene; a synthetic 3' UTR including a poly-A sequence; and a 5' UTR including an ARC-1 sequence element (which is complementary to an internal 18S rRNA segment, and may promote binding to the 40S ribosomal subunit); the Tobacco mosaic virus (TMV) 5'-UTR (omega sequence), which may be improved by adding a GAAAGA upstream of an initial GUA triplet.

In some embodiments, a DNA molecule is used to produce capped mRNA in vitro, for example, in the presence of the cap analog m7G[5']ppp[5']G. Non-incorporated nucleotides and cap analogs may be removed by gel filtration, and the purified mRNA may then be introduced into the cell-free system as described herein, where it serves as the template for polypeptide synthesis.

Monomers

In coupled IVTT reactions, ribonucleotide triphosphates (ATP, GTP, CTP, UTP) and amino acids are required in the system as the monomeric units used to synthesize the desired biopolymers. In some embodiments herein, the system operates with reduced levels of one or more NTPs relative to a comparable system with conventional energy regeneration system. In these embodiments, the disclosed system provides an advantageous reduced expense for the system's operation. In certain embodiments, the disclosed system operates with a final ATP concentration of between 2-10 mM, e.g., 4-8 mM or 5-7 mM ATP. In certain embodiments, the disclosed system operates with a final GTP concentration of between 0.8-2.5 mM, e.g., 1-2 mM or 1.4-1.8 mM GTP. In certain embodiments, the disclosed system operates with a final CTP concentration of between 0.4-2.4 mM, e.g., 0.5-2 mM or 0.6-1.0 mM CTP. Also, in certain embodiments, the disclosed system operates with a final UTP concentration of between 0.4-2.4 mM, e.g., 0.5-2 mM or 0.6-1.0 mM UTP. For example, the system can operate with final NTP concentrations at or about 6 mM ATP, 1.6 mM GTP, 0.8 mM CTP, and 0.8 mM UTP. In particular examples, a synthesis reaction is supplemented with low concentration NTP mix containing approximately 150 mM ATP, approximately 40 mM GTP, approximately 20 mM CTP, and approximately 20 mM UTP and the mix is added to the system in sufficient amount to provide the final concentration of NTPs. Amino acids may also be added, for example, to a final concentration of 20-500 pM. If a radiolabeled amino acid (e.g., $^{35}S$ methionine and $^{3}H$ leucine) is used in a coupled reaction, then the corresponding amino acid may be left out of the amino acid mix.

Salts

The concentration of salts is controlled in systems according to embodiments herein. For example, a system may have added to it one or more salts, including, for example, and without limitation, potassium, magnesium, ammonium, and other biologically relevant salts, such as manganese (e.g., of acetic acid or sulfuric acid). One or more of such salts may have amino acids as a counter anion. There is an interdependence among ionic species with regard to the function of the synthesis reaction. When changing the concentration of a particular ion in the reaction medium, that of another ion may be changed accordingly. For example, the concentrations of added salts may be simultaneously controlled in accordance with the change in other components, such as nucleotides. Furthermore, the concentration levels of components in a continuous-flow reactor may be varied over time.

Magnesium

Magnesium is important for protein translation, as it enhances ribosome assembly, and the stability of assembled ribosomes. Magnesium also appears to play a role in facilitating polymerase binding. In embodiments herein, the magnesium concentration of the cell lysate may be adjusted by an additional magnesium compound. In some embodiments, the additional magnesium compound is a salt; for example, magnesium chloride, magnesium acetate, and magnesium glutamate. For coupling transcription and translation, a sufficient amount of a magnesium salt may be added to the lysate to raise the final magnesium concentration to a level where RNA is transcribed from DNA, and RNA is translated into protein. In some examples, the final magnesium concentration may be adjusted to between 1-20 mM. For example, the final magnesium concentration may be between 5-15 mM, between 7-13 mM, between 2.5 mM and 5.5 mM, between 2.5 mM and 3.5 mM, between 2.6 mM and 3.0 mM, between 3.0 mM and 5.25 mM, or between 4.0 mM to 4.75 mM, depending on the lysate used.

To provide precise control of the magnesium concentration in a system herein, lysate magnesium levels may be measured directly through the use of a magnesium assay, prior to the addition of extra magnesium. The Lancer "Magnesium Rapid Star Diagnostic Kit" (Oxford LabWare-Division™, Sherwood Medical Co., St. Louis, Mo.), for example, is one assay that can accurately measure the magnesium levels in biological fluid. Once the magnesium ion concentration for a given batch of lysate is known, then additional magnesium may be added to bring the magnesium concentration of the lysate to within the desired range.

As suggested above, the final magnesium concentration in the reaction is affected by other conditions and considerations. Thus, for example, as the ribonucleotide triphosphate concentration goes up, there is a concomitant increase in the optimal magnesium concentration, as the ribonucleotide triphosphates tend to associate, or chelate, with magnesium in solution. Thus, when ribonucleotide triphosphate concentrations are increased, additional magnesium is generally also added to the reaction. The optimal concentration of magnesium also varies with the type of cellular lysate. The amount of magnesium required to be added also varies with the concentration of the lysate used in the reaction mixture, as increasing the concentration of the lysate will increase the contribution of magnesium from the lysate itself Potassium Potassium is also typically added to the system to achieve desired levels of biopolymer synthesis. Potassium (for example, potassium acetate and potassium glutamate) is generally present at a concentration of between 5-250 mM (e.g., 5-100 mM, 5-75 mM, 5-50 mM, and 5-30). In particular examples, the potassium concentration may be 10-20 mM, even more particularly it may be about 20 mM. As is the case for magnesium, the final potassium concentration may vary slightly, due to its presence in endogenous cellular lysate components.

Additional Components

Additional components may also be added to the system in particular embodiments, as desired for improving the efficiency or stability of the synthesis reaction. Although not absolutely necessary, one common addition to coupled transcription and translation reactions is an amount of a polyamine sufficient to stimulate the efficiency of chain elongation, for example. Polyamines affect optimal magnesium levels as well, and are known to lower the effective magnesium concentration for translation reactions somewhat. Thus, polyamines may substitute for magnesium at some level, and may permit some lowering of optimal magnesium levels for coupled transcription and translation in particular examples.

Metabolic inhibitors to undesirable enzymatic activity may be added to the reaction mixture. Alternatively, enzymes or factors that are responsible for undesirable activity may be removed directly from the extract or the gene encoding the undesirable enzyme may be inactivated or deleted from the chromosome.

Vesicles, either purified from the host organism (See Muller & Blobel (1984) Proc. Natl. Acad. Sci. U.S.A. 81:7421-5), or synthetic, may also be added to the system. These may be used to enhance protein synthesis and folding. For example, the systems described herein also may be used for cell-free reactions to activate membrane proteins; for example, to insert or translocate proteins or to translocate other compounds, and these processes may be aided in particular embodiments by the addition of vesicles containing desired membrane proteins.

In addition to the above components, other materials (such as those specifically utilized in protein synthesis) may be added to a system as described herein. Such materials may include, for example and without limitation, other salts, folinic acid, cyclic AMP, inhibitors of protein or nucleic acid degrading enzymes, RNasin, inhibitors or regulators of protein synthesis, adjusters of oxidation/reduction potential(s), DTT, chloramphenicol, non-denaturing surfactants, buffer components (such as may be used in the solution to stabilize the reaction pH), PEG, Triton X-100, spermine, spermidine, and putrescine.

Some embodiments include a kit including components of a system for synthesis of a biopolymer without using an artificial regeneration system. In particular embodiments, a kit may include a cell lysate. Alternatively, the kit may include cells for culture and expansion to yield cells for the preparation of a cell lysate. In particular embodiments, the kit may include one or more of salts, NTPs, enzymes (e.g., polymerases and nucleases), enzyme inhibitors (e.g., RNasin), template, and other additives (e.g., chloramphenicol). In particular examples, the kit may include a naked vector, into which may be cloned a gene of interest, for use as a template in the system. In kits including a cell lysate, the lysate may be standard, or it may be of the type where the adjustments to its salt concentrations have already been made during manufacture, or additionally where one or more of the components, reagents or buffers necessary for coupled transcription and translation have been included. In particular examples, the kit may not include a template, but instead may rely on the user to provide the template. A kit may comprise a set of instructions, or link to a website comprising instructions, informing the user how to utilize the components of the kit to perform a synthesis reaction.

V. Methods for Biopolymer Synthesis

The systems as described above may be used in a method for in vitro synthesis of one or more biopolymers. In vitro synthesis refers to the cell-free synthesis of biological macromolecules in a reaction mix comprising biological extracts and/or defined reagents. Using the systems herein, a cell-free synthesis reaction may be performed in batch, continuous flow, and semi-continuous flow configurations, as these configurations are known in the art. In some embodiments, batch-cultured cells may be used. In some embodiments, cells may be grown continuously in a stirred-tank fermenter to ensure a reproducible supply of homogeneous cell material.

There are differences between using a static IVTT reaction, versus a continuous or flow-through reactions, that may be a consideration in some applications, but not others. For example, the continuous system is generally used for large-scale industrial production of proteins, whereas static system reactions are better suited to small scale in vitro translations (e.g., in a research setting). Continuous translation is much more expensive to perform, requiring an investment in equipment, as well as significant amounts of reagents. In particular, the levels of RNA polymerases used to make continuous eukaryotic reactions work may be prohibitive for simple research applications (i.e., as much as 20,000-30,000 U/reaction). Furthermore, continuous reactions are designed to be performed in relatively large volumes, while static reactions require no extra equipment, and only small amounts of reagents, since the reaction volume is typically only on the order of 100 µL or less.

Systems herein may utilize a large scale reactor, a small scale reactor, or may be multiplexed to perform a plurality of simultaneous syntheses. Continuous reactions use a feed mechanism to introduce a flow of reagents, and may isolate the end-product as part of the process. In both continuous and static reactions, additional reagents may be introduced to prolong the period of time for active synthesis. A reactor may be run in any mode such as batch, extended batch, semi-batch, semi-continuous, fed-batch, and continuous, which mode may be selected in accordance with the application purpose.

Reactions may be conducted in any volume, again depending on the application and the equipment used. For example, in a small scale reaction, the reaction volume may be 1-15 µL, at least 15 µL, at least 50 µL, at least 100 µL, at least 0.5 mL, or at least 1 mL, but may be less than 10 mL. In principle, reactions may be conducted at any scale as long as sufficient oxygen (or other electron acceptor) is supplied. For production of the largest amount of product, industrial bioreactors may be used.

Methods herein may utilize a means for isolating the synthesized biopolymer; for example, a protein isolating means. In some embodiments operated in a continuous operation mode, the product output from the reactor flows through a membrane, and into the protein isolating means. In a semi-continuous operation mode, the outside or outer surface of the membrane is put into contact with predetermined solutions that are cyclically changed in a predetermined order. These solutions may contain substrates such as amino acids and nucleotides. At this time, the reactor is operated in dialysis, or diafiltration batch or fed-batch mode. A feed solution may be supplied to the reactor through the same membrane or a separate injection unit. Synthesized protein is accumulated in the reactor, and then is isolated and purified according to the usual method for protein purification after completion of the system operation.

Where there is a flow of reagents, the direction of liquid flow can be perpendicular and/or tangential to a membrane. Tangential flow is effective for recycling ATP, and for preventing membrane plugging and may be superimposed on perpendicular flow. Flow perpendicular to the membrane may be caused or effected by a positive pressure pump or a vacuum suction pump. The solution in contact with the outside surface of the membrane may be cyclically changed, and may be in a steady tangential flow with respect to the membrane. Furthermore, the reactor may be stirred internally or externally by proper agitation means.

During protein synthesis in the reactor, the protein isolating means for selectively isolating the desired protein may include a unit packed with particles coated with antibody molecules or other molecules immobilized with a component for adsorbing the synthesized, desired protein, and a membrane with pores of proper sizes. Preferably, the protein isolating means comprises two columns for alternating use.

The amount of protein produced in a translation reaction can be measured in various fashions. One method relies on the availability of an assay which measures the activity of the particular protein being translated. An example of an assay for measuring protein activity is a luciferase assay system, or chloramphenicol acetyltransferase assay system. These assays measure the amount of functionally active protein produced from the translation reaction. Activity assays will not measure full length protein that is inactive due to improper protein folding or lack of other post-translational modifications necessary for protein activity. Alternatively, specific proteins might be detected according to their size by capillary electrophoresis.

Another method of measuring the amount of protein produced in coupled in vitro transcription and translation reactions is to perform the reactions using a known quantity of radiolabeled amino acid such as $^{35}$S-methionine, $^{3}$H-leucine, or $^{14}$C-leucine, and subsequently measure the amount of radiolabeled amino acid incorporated into the newly translated protein. Incorporation assays will measure the amount of radiolabeled amino acids in all proteins produced in the reaction, including truncated protein products. The radiolabeled protein may be further separated on a protein gel, and by autoradiography confirmed that the product is the proper size, and that secondary protein products have not been produced.

EXAMPLES

Example 1: Materials and Methods

Plant Material

Tobacco cells (*Nicotiana tabacum* L. cv. Bright Yellow 2, BY-2) were cultivated in a 5-L fermenter (Type 100e, Applicon™ Biotechnology, AC Schiedam, Netherlands) or shake flask while maintaining a packed cell volume of 20-25% at 26° C. in the dark. We used Murashige-Skoog liquid medium (Murashige and Skoog basal salt mixture, Duchefa™ Biochemie, Haarlem, Netherlands) supplemented with 3% (w/v) sucrose, 1 mg/L thiamine-HCl, 0.2 mg/L 2,4 dichlorophenoxyacetic acid, 100 mg/L myo-inositol, 250 mg/L potassium dihydrogen orthophosphate, and Pluronic® L-61 antifoam (BASF™, Mount Olive, N.J., USA).

Preparation of the BY-2 Cell Lysate

BY-2 cells were harvested during the exponential growth phase of a fermentation at a constant packed cell volume of 20-25%. To prepare protoplasts, they were treated with 3% (v/v) Rohament® CL and 0.2% (v/v) Rohapect® UF (pectinase and arabanase) (AB Enzymes™, Darmstadt, Germany) directly in the fermentation medium. The osmolarity was adjusted by addition of 360 mM mannitol.

To evacuolate the resulting protoplasts, the protoplasts were layered onto a discontinuous Percoll gradient containing (from bottom to top) 70% (v/v, 3 ml), 40% (v/v, 5 ml), 30% (v/v, 3 ml), 15% (v/v, 3 ml) and 0% (3 ml) Percoll (GE™ Healthcare, Munich, Germany) in 0.7 M mannitol, 20 mM MgCl$_2$ and 5 mM PIPES-KOH (pH 7.0) in a 50 mL polypropylene tube (Greiner Bio-One™, Frickenhausen, Germany). After centrifugation at 6800×g for 1 h at 25° C. in a swinging-bucket rotor (JS-5.3, Beckmann-Coulter™, Krefeld Germany), evacuolated protoplasts were recovered from the 40-70% (v/v) Percoll solution interface, and suspended in 3-3.5 volumes of TR buffer (30 mM HEPES-KOH (pH 7.4), 60 mM potassium glutamate, 0.5 mM magnesium glutamate, 2 mM DTT), supplemented with one tablet per 50 mL of Complete EDTA-free Protease Inhibitor Mixture (Roche Diagnostics™, Mannheim, Germany).

The protoplasts were then disrupted on ice using 15 strokes of a Dounce™ homogenizer (Braun™, Melsungen, Germany), and the nuclei and non-disrupted cells were removed by centrifugation at 500×g for 10 minutes at 4° C. The supernatant was then frozen in 1 mL aliquots at −80° C. Optionally and prior to freezing, the supernatant can be supplemented with 0.5 mM CaCl$_2$ and treated with 75 U/mL nuclease S7 (Roche Diagnostics) for 15 minutes at 20° C., and then be supplemented with 2 mM EGTA as a chelating agent for the Ca$^{2+}$ ions to inactivate the nuclease.

Plasmid Constructs

Vector pIVEX_GAAAGA_Omega_eYFP-His was prepared by inserting annealed oligonucleotide primer 1 (SEQ ID NO:1) and oligonucleotide primer 2 (SEQ ID NO:2) containing the T7 promoter and the Tobacco mosaic virus 5' omega leader sequence with GAAAGA as the first six nucleotides into pIVEX1.3_eYFP-His (kindly provided by Dr. Stefan Kubick, Fraunhofer Institute for Cell Therapy and Immunology IZI, Potsdam-Golm, Germany) using the NspI and NcoI sites. For vector pIVEX_GAAAGA_Omega_S-trep-eYFP containing an N-terminal streptavidin affinity tag, the Strep-eYFP sequence was amplified by PCR using pIX3.0_Strep-eYFP as a template (kindly provided by Dr. Stefan Kubick) with oligonucleotide primer 3 (SEQ ID NO:3) and oligonucleotide primer 4 (SEQ ID NO:4). The PCR product was digested with PciI and Acc65I and inserted into the NcoI and Acc65I sites of pIVEX_GAAAGA_Omega_eYFP-His.

The pIVEX vectors with 21333, 22807, AAD12, Cry2A, Cry3A, Trap8VIP3A, VIP3A, Cry6A, 17912, and Cry1F were created by PCR amplification of the genes using oligonucleotide primers 5-24 (SEQ ID NOs:5-24) and subsequent integration of the PCR products into pIVEX_GAAAGA_Omega_eYFP-His cut with NcoI and KpnI by Gibson assembly (NEB™, Frankfurt, Germany).

TABLE 1

Oligonucleotide primers and vector inserts.

| Primer No. | Nucleotide sequence (5'→3') |
|---|---|
| 1 | TAATACGACTCACTATAGAAAGAGTATTTTTACAACAATTACCAACAACAACAACAAACAACAACAACATTACATTTTACATTCTACAACTAC (SEQ ID NO: 1) |
| 2 | CATGGTAGTTGTAGAATGTAAAATGTAATGTTGTTGTTGTTTGTTGTTGTTGTTGGTAATTGTTGTAAAAATACTCTTTCTATAGTGAGTCGTATTACATG (SEQ ID NO: 2) |
| 3 | GATCATACATGTGGTCTCATCCGCAATTC (SEQ ID NO: 3) |
| 4 | GATCATGGTACCTTATTACTTGTACAGCTCGTCC (SEQ ID NO: 4) |
| 5 | CAACAACATTACATTTTACATTCTACAACTACATGAATCAAAATAAACACGGAATTATTGGC (SEQ ID NO: 5) |
| 6 | GTCCAAACCAAACCAGAAGAGCTGGGTACCCTATTACTTTTCTGTTTCAACGAATTCAAT (SEQ ID NO: 6) |
| 7 | CAACAACATTACATTTTACATTCTACAACTACATGAATAATGTATTGAATAGTGGAAGAACAAC (SEQ ID NO: 7) |
| 8 | GTCCAAACCAAACCAGAAGAGCTGGGTACCCTATTAATAAAGTGGTGAAATATTAGTTGG (SEQ ID NO: 8) |
| 9 | CAACAACATTACATTTTACATTCTACAACTACATGGCTCAGACCACTCTCCAAATCACAC (SEQ ID NO: 9) |
| 10 | GTCCAAACCAAACCAGAAGAGCTGGGTACCTTATCAAACCAAGGCAGCACCCTCAGTT (SEQ ID NO: 10) |
| 11 | CAACAACATTACATTTTACATTCTACAACTACATGAACAATGTGCTGAACTCTGGTCG (SEQ ID NO: 11) |
| 12 | GTCCAAACCAAACCAGAAGAGCTGGGTACCCTATCAGTAGAGGGGAGGAAGGTTGGTC (SEQ ID NO: 12) |
| 13 | CAACAACATTACATTTTACATTCTACAACTACATGAATCCGAACAATCGAAGTGAACATGA (SEQ ID NO: 13) |
| 14 | TCCAAACCAAACCAGAAGAGCTGGGTACCTCATTAATTCACTGGAATAAATTCAATTTTG (SEQ ID NO: 14) |
| 15 | CAACAACATTACATTTTACATTCTACAACTACATGGCCCAGTCTAGCCGCATCTGC (SEQ ID NO: 15) |
| 16 | TCCAAACCAAACCAGAAGAGCTGGGTACCCTATCACTTGATCGAGAAATCGCGAAAGTTG (SEQ ID NO: 16) |
| 17 | CAACAACATTACATTTTACATTCTACAACTACATGAATATGAATAATACTAAATTAAACGCAAGG (SEQ ID NO: 17) |
| 18 | GTCCAAACCAAACCAGAAGAGCTGGGTACCTCATTACTTAATTGAAAAATCTCGGAAATT (SEQ ID NO: 18) |
| 19 | CAACAACATTACATTTTACATTCTACAACTACATGATTATTGATAGTAAACGACTTTACCTAGAC (SEQ ID NO: 19) |
| 20 | TCCAAACCAAACCAGAAGAGCTGGGTACCTCATTAATTATTATACCAATCCGAATTATTA (SEQ ID NO: 20) |
| 21 | CAACAACATTACATTTTACATTCTACAACTACATGTACACAAGTATTTATAAATTAGAGG (SEQ ID NO: 21) |
| 22 | GTCCAAACCAAACCAGAAGAGCTGGGTACCCTATTACTCTTTTTTGTCATTATGTTGATT (SEQ ID NO: 22) |
| 23 | CAACAACATTACATTTTACATTCTACAACTACATGGAAAATAATATTCAAAATCAATGCGTAC (SEQ ID NO: 23) |
| 24 | GTCCAAACCAAACCAGAAGAGCTGGGTACCCTATTATTCCTCCATAAGAAGTAATTCCAC (SEQ ID NO: 24) |

Coupled Transcription-Translation Cell-Free Protein Synthesis

Coupled transcription-translation reactions were carried out in 50 µL aliquots at 25° C. and 700 rpm for 40-52 hours in a thermomixer (HLC by Ditabis™, Pforzheim, Germany). Reactions with creatine phosphate and creatine kinase contained 40% (v/v) tobacco BY-2 cellular lysate (BYL), 20 mM HEPES-KOH pH 7.8, 10 mM magnesium glutamate, 10 mM potassium glutamate, 3 mM ATP, 1.2 mM GTP, 1.2 mM CTP, 1.2 mM UTP, 100 µg/mL chloramphenicol, 50 ng/µL T7 RNA polymerase, 80 ng/µl plasmid, 30 mM creatine phosphate and 100 µg/ml creatine kinase. Reactions without creatine phosphate and creatine kinase contained 40% (v/v) BYL, 20 mM HEPES-KOH (pH 7.8), 9 mM magnesium glutamate, 20 mM potassium glutamate, 4 mM ATP, 1.6 mM GTP, 1.6 mM CTP, 1.6 mM UTP, 100 µg/mL chloramphenicol, 30 ng/µL T7 RNA polymerase, and 40 ng/µL plasmid.

Product Analysis

The fluorescent signal from eYFP was quantified using a Synergy™ HT Multi-Mode Microplate Reader (Biotek™, Bad Friedrichshall, Germany) with 485/20 nm excitation and 528/20 nm emission filters. The quantity of eYFP was determined by generating a standard curve based on different concentrations of eYFP in BYL translation reactions without a DNA template. The eYFP standard was produced using an in-house in vitro translation system based on *E. coli* (Zawada (2012) Methods Mol. Biol. 805:31-41), and purified by immobilized metal-affinity chromatography (IMAC) and size-exclusion chromatography (SEC). The concentration of purified eYFP was determined using a colorimetric assay. Bradford (1976) Anal. Biochem. 72: 248-54.

Residue-Specific Labeling of Target Proteins

In order to label target proteins fluorescently in an amino acid selective manner the FluoroTect™ GreenLys in vitro Translation Labeling System (Promega™, Mannheim, Germany) was used according to the manufacturer's instructions. The product contains a modified charged lysine tRNA labeled with the fluorophore BODIPY®-FL. Using this system, fluorescently labeled lysine residues are incorporated into nascent proteins at multiple sites during translation.

JC-1 Staining

The presence of mitochondria in the BYL was proven using the lipophilic cationic probe 5,6-dichloro-2-[3-(5,6-dichloro-1,3-diethyl-1,3-dihydro-2H-benzimidazol-2-ylidene)-1-propenyl]-1,3-diethyl-iodide (JC-1, Thermo Scientific™, Waltham, Mass., USA). In living cells, JC-1 exists as a green fluorescent monomer (490 nm excitation/530 nm emission) at depolarized mitochondrial membrane potentials. At normal and hyperpolarized mitochondrial membrane potentials, JC-1 is concentrated inside mitochondria and forms J aggregates, which shift the emission from 530 to 590 nm. Cell mitochondria demonstrate increasingly higher red fluorescence (590 nm) of J aggregates with increasingly negative mitochondrial membrane potential. Nuydens et al. (1999) J. Neurosci. Methods 92:153-9; Reers et al. (1995) Methods Enzymol. 260:406-17; Salvioli et al. (1997) FEBS Lett. 411:77-82.

For BYL staining, JC-1 was dissolved in DMSO at a concentration of 5 mg/mL. The JC-1 stock solution was used in 1:1000 dilution for staining mitochondria within 10 minutes at a final concentration of 5 µg/mL.

Cell-Free Protein Synthesis with Inhibitors for Oxidative Phosphorylation.

Cell-free protein synthesis (50 µL reactions) was carried out with and without addition of an inhibitor of oxidative phosphorylation to the BYL systems both with and without creatine phosphate and creatine kinase. Inhibitors included: sodium azide (0.05%, Bogucka & Wojtczak (1966) Biochim. Biophys. Acta 122:381-92) and 2-thenoyltrifluoroacetone (TTA, 0.5 mM; Tappel (1960) Biochem. Pharmacol. 3:289-96). Sodium azide was solubilized in water. TTA was solubilized in methanol. Negative controls performed with methanol demonstrated that this solvent did not affect protein synthesis at concentrations used in this study.

Example 2: Protein Synthesis without Artificial Energy Regeneration

To reduce the release of phosphate, the artificial regeneration system consisting of creatine phosphate (CP) and creatine kinase (CK) was omitted in the cell-free BYL system. Reactions with variable concentrations of the reaction components were devised utilizing Design Of Experiment (DoE)-based approaches (fractional designs and response surface models in Design Expert v8.0 (StateEase™ Inc., MN, USA)), with and without CP and CK; HEPES-KOH, pH 7.8 (0-80 mM), magnesium glutamate (1-12 mM), potassium glutamate (0-40 mM), plasmid (10-100 ng/µL (4.5-43 nM)), NTPs (i.e., ATP/(GTP/CTP/UTP)) (0.5/0.2-4/1.6 mM), and T7 RNA polymerase (20-80 ng/µL), with and without CP (0-40 mM) and CK. The concentration of chloramphenicol was adopted from the system with CP/CK. From these experiments, preferred reaction component concentrations were obtained for both systems (with and without CP/CK). Table 2.

TABLE 2

Preferred concentrations of reaction components in the coupled BYL system, with and without CP/CK.

| Component | +CP/CK | −CP/CK |
|---|---|---|
| HEPES-KOH, pH 7.8 | 20 mM | 20 mM |
| Magnesium glutamate | 10 mM | 9 mM |
| ATP/(GTP/CTP/UTP) | 3/1.2 mM | 4/1.6 mM |
| Creatine phosphate | 30 mM | — |
| Plasmid | 80 ng/µL (~34 nM) | 40 ng/µl (~17 nM) |
| T7 polymerase | 50 ng/µL | 30 ng/µl |
| Potassium glutamate | 10 mM | 20 mM |
| Creatine kinase | 100 µg/mL | — |
| Chloramphenicol | 100 µg/mL | 100 µg/mL |

Figure 1B:
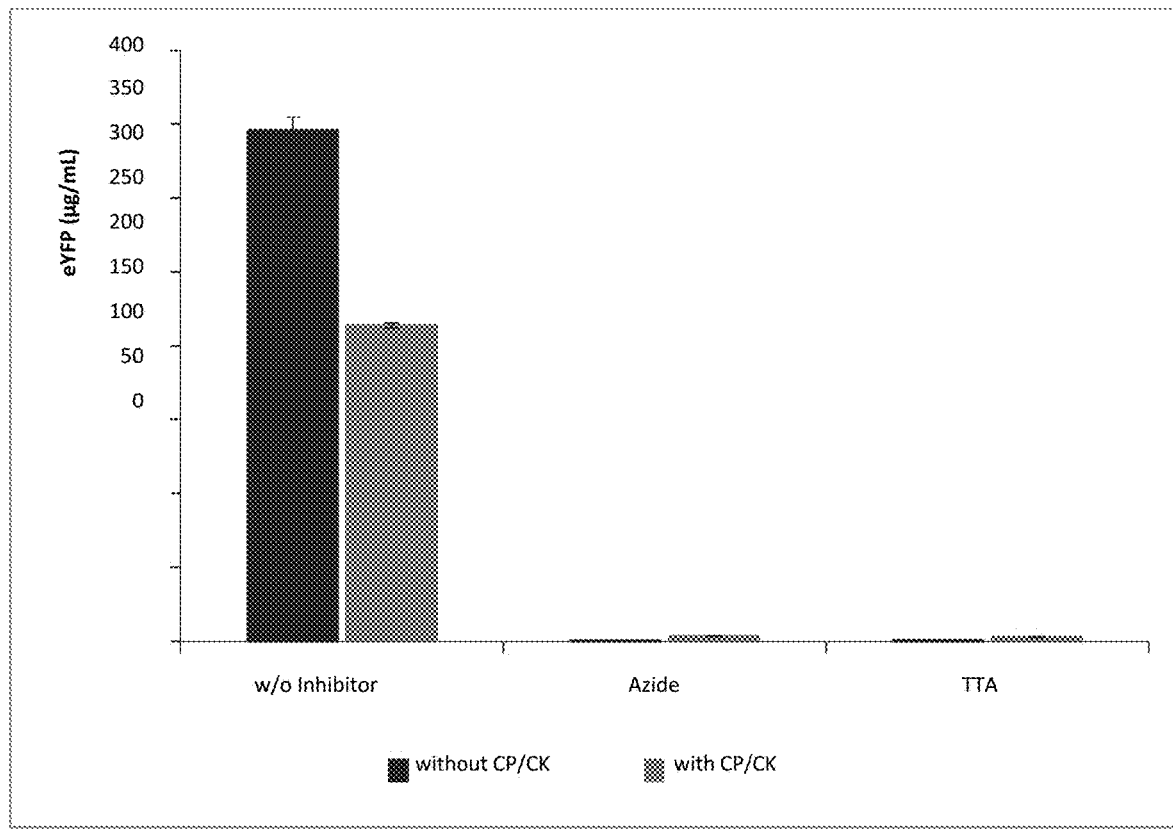

The comparison of the BYL system, with CP/CK and without CP/CK, revealed that the system without CP/CK showed a prolonged activity for around 40 hours (compared to 20 hours in BYL with CP/CK), and yielded up to 60% more target protein. FIG. 1A. The presence of mitochondria in the BYL was proven by staining BYL with a selective dye JC-1 (Thermo Fischer Scientific, Waltham, Mass., USA) that fluoresced red, indicating that the mitochondria retained their characteristic membrane potential in BYL. The energy regeneration by oxidative phosphorylation was demonstrated by the use of two different inhibitors of the electron transport chain; sodium azide and thenoyltrifluoroacetone (TTA). Both sodium azide and TTA were found to inhibit the system almost completely, as shown by the drastically reduced biosynthesis of the target protein, eYFP. FIG. 1(B).

Figure 2:
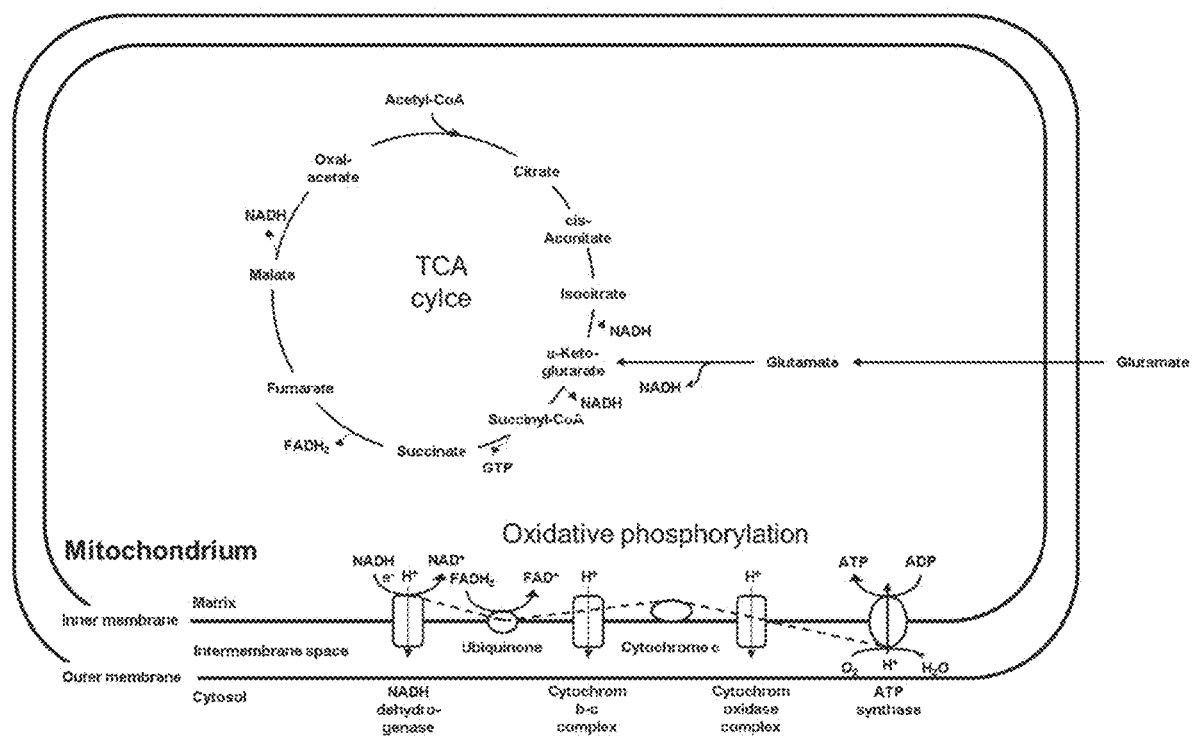
FIG. 2 includes a diagram representing the proposed mechanism of ATP generation in a system for synthesis without using artificial energy regeneration. Glutamate is used as an energy source to produce reducing equivalents, primarily in the form of NADH, through the TCA cycle located inside the mitochondria. NADH fuels oxidative phosphorylation, in which oxygen serves as the final electron acceptor, and ADP is converted into ATP.

The energy in the system without CP/CK is believed to be provided by oxidative phosphorylation. Glutamate derived from the added magnesium glutamate and potassium glutamate is metabolized in the citrate cycle inside the mitochondria, resulting in the generation of the reducing equivalents, NADH and FADH. Electrons enter the electron transport chain via NADH and FADH to generate ATP through oxidative phosphorylation by consumption of molecular oxygen. FIG. 2.

The expression of ten target proteins in the BYL system without CP/CK was compared to the BYL system with CP/CK. Coupled BYL transcription-translation reactions with and without creatine phosphate (CP) and creatine kinase (CK) were carried out at 25° C. for 40 hours. In each case, 2 μL reaction volume was loaded on a 4-12% (w/v) gradient SDS-PAGE gel and the amounts of synthesized proteins were visualized by Coomassie staining. Several target proteins, including AAD12, Cry3A, and Cry1F, showed a significantly higher expression level in the optimized system (without CP/CK), as represented by the stronger bands in the Coomassie-stained gel.

The BYL system without an artificial energy regeneration system is cheaper and runs longer leading to increased levels of the recombinant protein. Moreover, the BYL system offers the possibility to investigate compounds or proteins affecting mitochondrial functions.

Example 3: Modifications of Coupled Transcription-Translation Reactions without Artificial Energy Regeneration Use of Sorbitol for BY-2 Lysate Preparation.

Figure 5:
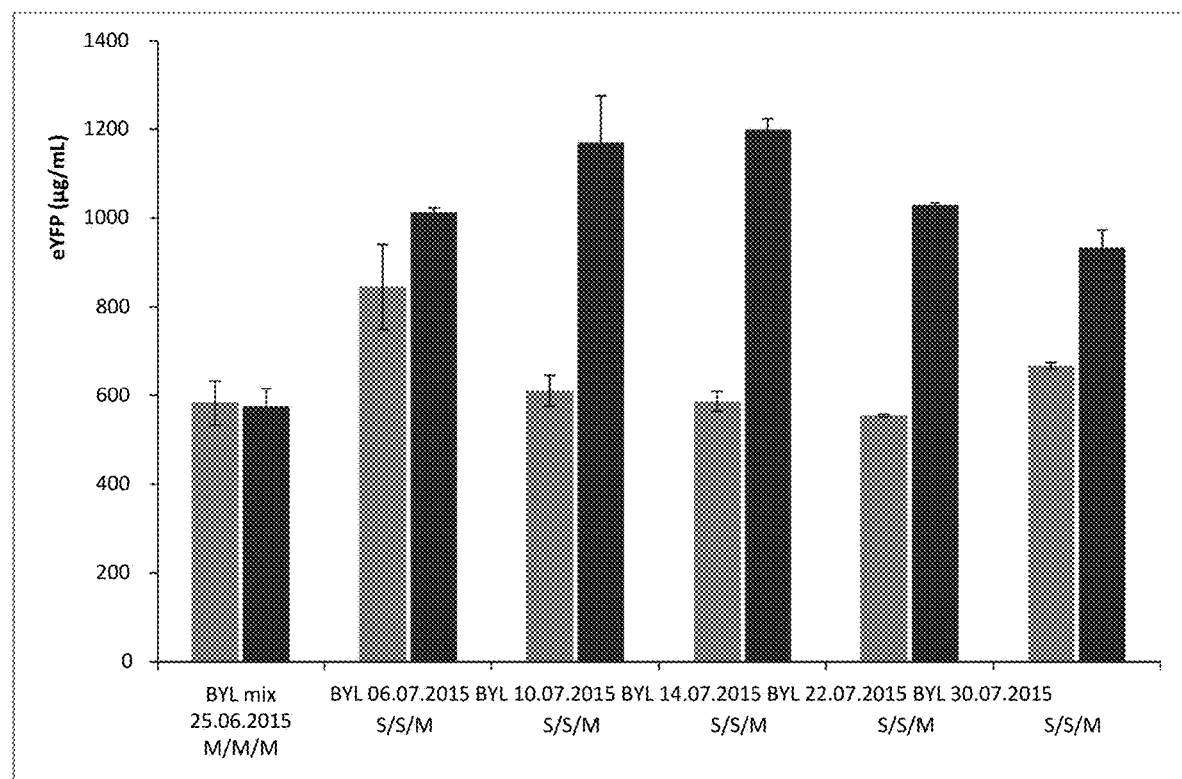
FIG. 5 includes a bar graph showing the effects of increasing lysate concentrations on productivity in a system for synthesis without using artificial energy regeneration. Reactions with the BY-2 cell lysate prepared with mannitol ("BYL mix") were compared to reactions with the new lysates prepared with sorbitol ("BYL 06.07.2015", "BYL 10.07.2015"; "BYL 14.07.2015"; "BYL 22.07.2015"; "BYL 30.07.2015"). Reactions were performed in a volume of 50 µL in 96-well plates. Light bars represent 40% (v/v) lysate reactions, and dark bars represent 60% (v/v) lysate reactions. "M" and "S" designate the use of mannitol and sorbitol, respectively, for protoplastation, evacuolation, and washing of evacuolated protoplasts during lysate preparation. Coupled reactions were carried out using pIVEX_GAAAGA_Omega_Strep-eYFP as the DNA template at 25° C. and 700 rpm for 48 hours. The yield of eYFP was determined by measuring fluorescence intensity using a fluorescence reader. Means and standard deviations were calculated from two independent experiments. Dates indicate the day of merging of the large "BYL mix," and the day of preparation for each new lysate, respectively.

For the preparation of the BY-2 lysate large amounts of an osmolar substance are needed to adjust the osmolarity during protoplastation and evacuolation. Mannitol is routinely used for this purpose, and it accounts for about 10% of the total cost of lysate preparation. We tested the ability of sorbitol (around 10 times cheaper) as an osmolar substance. Parallel experiments using mannitol or sorbitol for protoplastation and evacuolation revealed that sorbitol is surprisingly not an equivalent of mannitol; it is superior with regard to both lysate yield and lysate quality as determined by the expression of eYFP (FIG. 5). Moreover, the higher solubility of sorbitol was found to facilitate buffer preparation. However, it was also found that mannitol is superior to sorbitol for the final washing of the evacuolated protoplasts, as utilization of sorbitol in this step leads to lower eYFP yield and to a more viscous reaction mix.

Inhibition of Microbial Growth.

BY-2 lysate is capable of supporting growth of microorganisms when IVTT reactions are incubated, resulting in depletion of reaction substrates and consequent reduced yield of target protein. Therefore, several antimicrobial substances were tested in the IVTT reaction system. Chloramphenicol, spectinomycin, streptomycin, ampicillin, and sodium azide were investigated with respect to their effect on IVTT eYFP production and microbial growth.

Figure 3A:
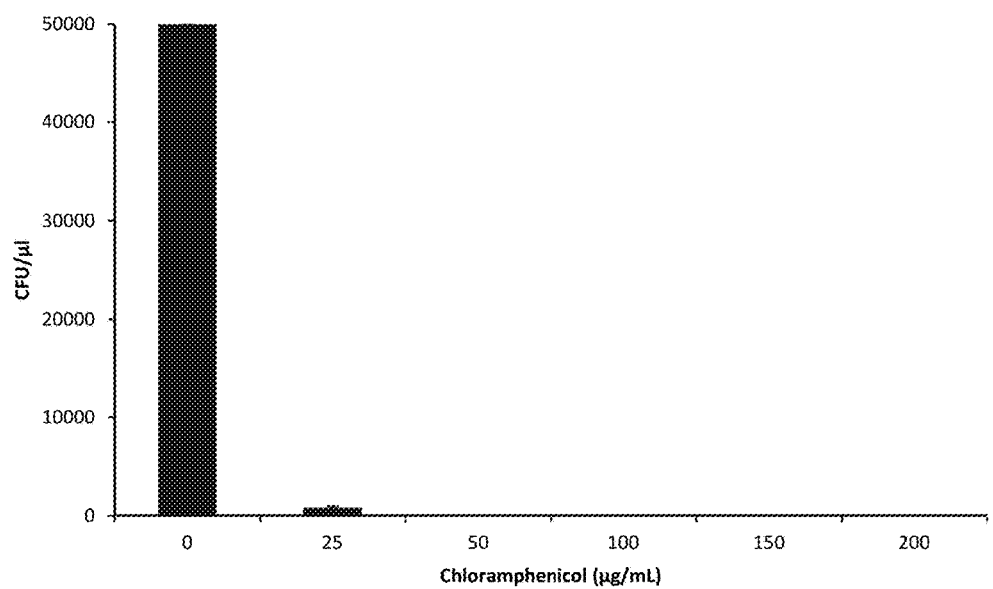
FIG. 3A-3D includes charts showing effects of different antimicrobial substances on eYFP yield and microbial growth in a system for synthesis without using artificial energy regeneration. Coupled BYL reactions were carried out using pIVEX_GAAAGA_Omega_Strep-eYFP as the template at 25° C. and 700 rpm for 45 hours. The yield of eYFP was determined by measuring fluorescence intensity using a fluorescence reader. The number of colony forming units (CFUs) was determined by plating out 0.2 µL BYL reaction volume on LB plates, which were then incubated at 37° C. for 16 hours. Means and standard deviations were calculated from three independent experiments.
Figure 3B:
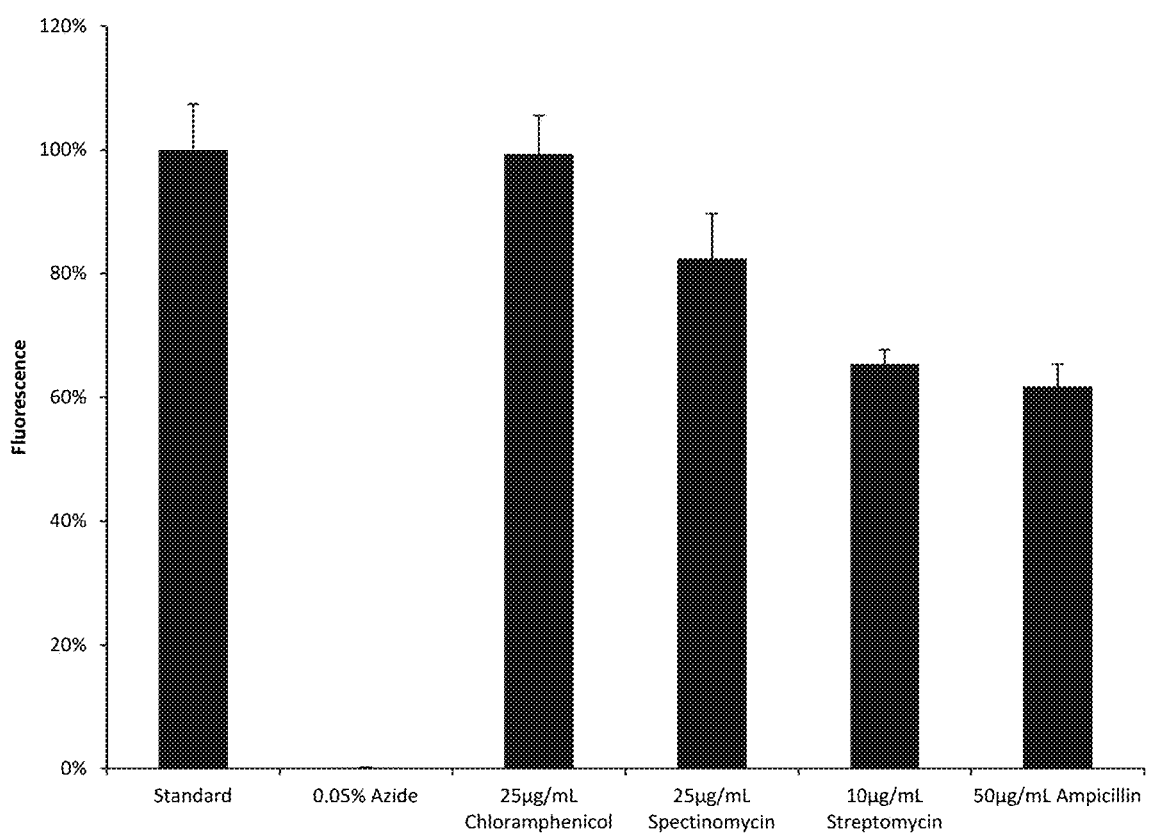
Figure 3C:
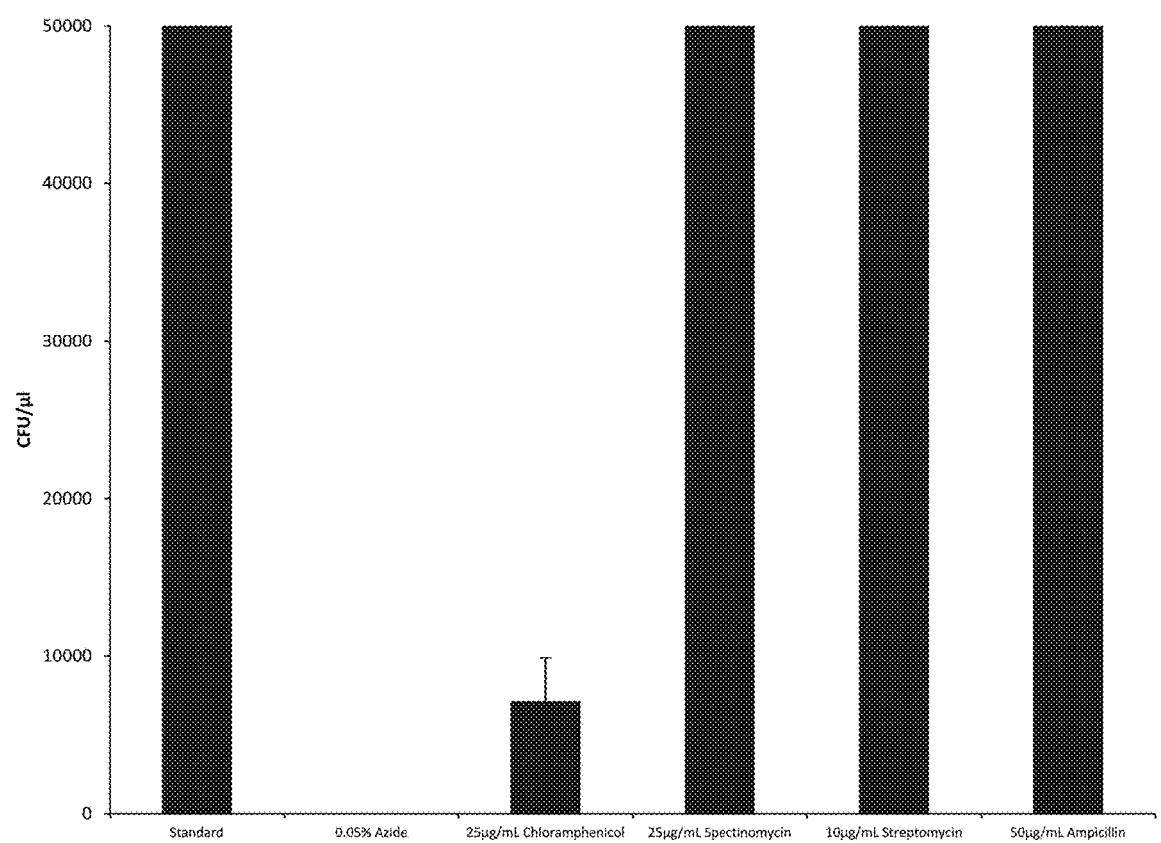
Figure 3D:
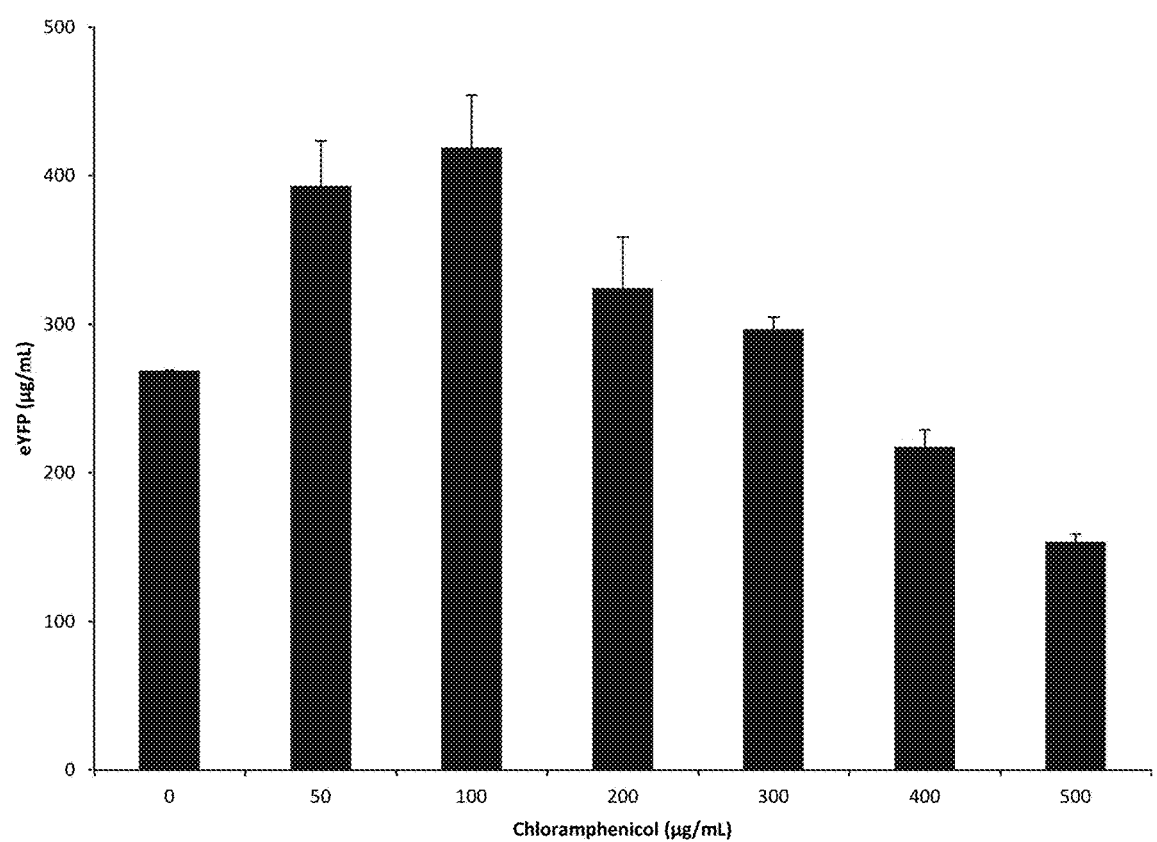

Antimicrobial substances were added to BYL reactions, and after 45 hours incubation, 0.2 μL BYL reaction mix was plated on LB plates to analyse microbial growth. Spectinomycin, streptomycin, ampicillin, and sodium azide had either no inhibiting effect on microbial growth, or else showed an adverse impact on the eYFP yield. For example, sodium azide at a concentration of 0.05% (w/v) inhibited both microbial growth and translational activity almost completely, possibly by inhibiting mitochondrial energy regeneration. Only chloramphenicol was able to inhibit microbial growth without any loss of translational activity (FIG. 3B; FIG. 3C), thereby making it unlike at least the other antimicrobial substances in its usefulness in the IVTT system. Dose response studies indicated that the highest eYFP yield was achieved at 100 μg/mL chloramphenicol (FIG. 3D, while complete inhibition of microbial growth was obtained at 200 μg/mL chloramphenicol (FIG. 3A) SDS-PAGE analysis also demonstrated the protective effect of chloramphenicol on eYFP yield and protein stability. Unlike reactions performed in the presence of chloramphenicol, reactions without chloramphenicol showed significant protein degradation.

Nucleoside Triphosphates.

The concentrations of the NTPs in the system were adjusted by a DoE-based approach. Since ATP and GTP are used in both transcription and translation, whereas CTP and UTP are only used in transcription, higher concentrations of ATP and GTP compared to CTP and UTP were expected to be beneficial for the coupled IVTT system. Therefore, the concentrations of the single NTPs were varied in the DoE-based experiment, instead of using different volumes of a fixed NTP mix. These were screened for optimal concentrations using a cubic IV-optimal design with 96 runs. The plasmid template for the IVTT reaction was pIVEX_GAAAGA_Omega_Strep-eYFP. The concentration of magnesium glutamate was adjusted, due to the binding of NTPs to magnesium. Table 3 shows the concentration ranges for each of the screened factors. A quadratic model was fitted onto the experimental data. Response surface models were used to predict the factor values yielding the most product eYFP protein (Zhou et al., 2010). All non-significant terms ($p>0.05$ by ANOVA) were dropped, and the model was shown in the ANOVA table to be significant (Table 4).

Figure 4A:
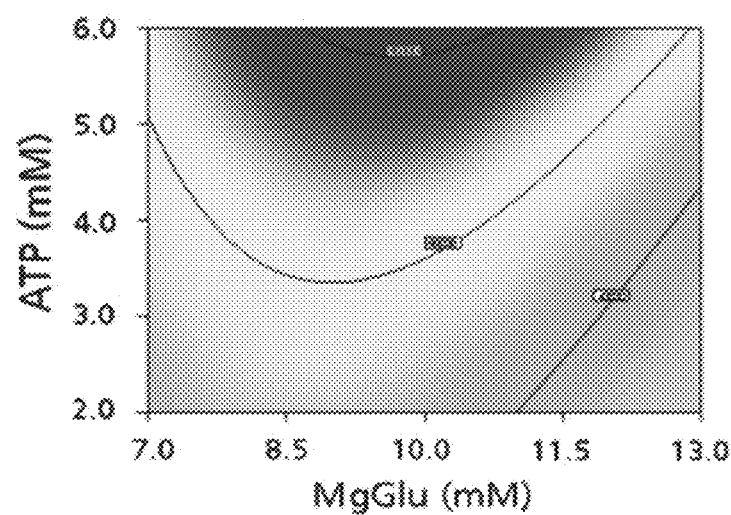
FIG. 4A-4C includes a visual representation of the DoE-based optimization of the NTP mixture used in a system for synthesis without using artificial energy regeneration. Presented are the response surface and contour plots for eYFP synthesis in a coupled BYL system without creatine phosphate and creatine kinase. The effect of different NTPs and magnesium glutamate on the yield is shown, while the other components of the reaction volume are maintained at optimal concentrations. The plots show significant interactions between magnesium glutamate and ATP (FIG. 4(A)), between magnesium glutamate and GTP (FIG. 4(B)), and between magnesium glutamate and CTP/UTP (FIG. 4(C)). Reactions were carried out using the plasmid pIVEX_GAAAGA_Omega_Strep-eYFP as the DNA template at 25° C. and 700 rpm for 46 hours. The yield of eYFP (given in relative fluorescent units, RFU) was determined by measuring fluorescence intensity using a fluorescence reader.
Figure 4B:
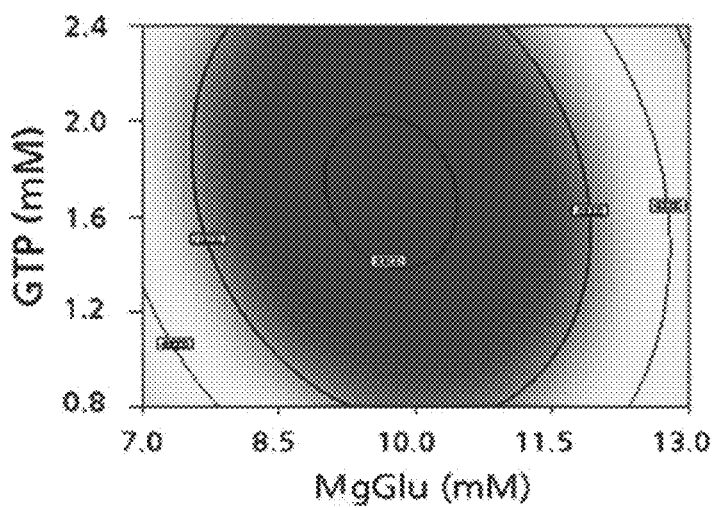
Figure 4C:
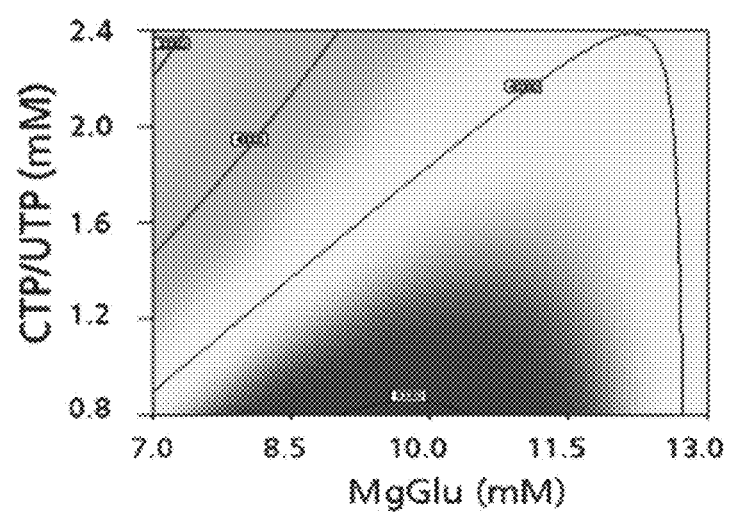

The experiment revealed that the most target protein is produced with 6 mM ATP, 0.8 mM CTP, 0.8 mM UTP, and 1.6 mM GTP in the reaction. FIG. 4. These results led to the development of a new NTP mix consisting of 150/40/20/20 mM ATP/GTP/CTP/UTP. Using 2 μL new NTP mix increased eYFP yield by 20% in the IVTT system. As an additional benefit, the new NTP mix costs approximately 40% less than the standard mix, due to the 10-15 fold lower cost of ATP, as compared to the other nucleotides.

TABLE 3

Concentration ranges for factors screened in the experimental design.

| Factor | Concentrations |
| --- | --- |
| Magnesium glutamate | 7-13 mM |
| ATP | 2-6 mM |
| GTP | 0.8-2.4 mM |
| CTP/UTP | 0.8-2.4 mM |

TABLE 4

ANOVA table for yield as a function of magnesium glutamate and NTP concentrations.

| Source | Sum of squares | Degrees of freedom | Mean squares | F value | p-value Prob > F |
| --- | --- | --- | --- | --- | --- |
| Model | 124514.3 | 11 | 11319.49 | 17.99406 | 2.2E−17 |
| A (Mg-glutamate) | 7628.711 | 1 | 7628.711 | 12.12701 | 0.000808 |
| B (ATP) | 13592.04 | 1 | 13592.04 | 21.60664 | 1.3E−05 |

TABLE 4-continued

ANOVA table for yield as a function of magnesium glutamate and NTP concentrations.

| Source | Sum of squares | Degrees of freedom | Mean squares | F value | p-value Prob > F |
|---|---|---|---|---|---|
| C (GTP) | 10851.73 | 1 | 10851.73 | 17.2505 | 8.14E−05 |
| D (CTP/UTP) | 6002.224 | 1 | 6002.224 | 9.541457 | 0.002762 |
| AB | 6051.846 | 1 | 6051.846 | 9.620339 | 0.002658 |
| AC | 1801.49 | 1 | 1801.49 | 2.863746 | 0.094488 |
| AD | 28988.81 | 1 | 28988.81 | 46.08216 | 1.8E−09 |
| BC | 4963.614 | 1 | 4963.614 | 7.890426 | 0.006244 |
| BD | 12477.49 | 1 | 12477.49 | 19.83488 | 2.71E−05 |
| $A^2$ | 23554.84 | 1 | 23554.84 | 37.44404 | 3.29E−08 |
| $C^2$ | 3093.903 | 1 | 3093.903 | 4.918233 | 0.029411 |
| Residual | 50325.43 | 80 | 629.0679 | | |
| Lack of Fit | 43891.77 | 69 | 636.1126 | 1.087598 | 0.472983 |
| Pure Error | 6433.661 | 11 | 584.8782 | | |
| Cor Total | 174839.8 | 91 | | | |
| Std. Dev. | 25.08123 | R-Squared | | 0.712163 | |
| Mean | 209.8901 | Adj R-Squared | | 0.672585 | |
| C.V. % | 11.94969 | Pred R-Squared | | 0.613957 | |
| PRESS | 67495.66 | Adeq Precision | | 20.54854 | |

Use of Larger Lysate Quantities.

To investigate the effect of increasing the lysate portion of the IVTT reaction on target protein expression, 50 μL reactions with 40% (20 μL) or 60% (30 μL) lysate were performed using the BYL prepared with mannitol, as well as with several BY-2 lysates prepared with sorbitol during protoplastation and evacuolation. Using plasmid pIVEX_GAAAGA_Omega_Strep-eYFP as the template, reactions were carried out at 25° C. and 700 rpm for 48 hours. The reactions with 60% (v/v) of the sorbitol-prepared lysates achieved around 1 mg/mL eYFP, which corresponds to an 80% higher yield compared to the standard reaction mix (FIG. 5). Presumably, the increased abundance of ribosomes, translation factors, chaperones, and mitochondria increased or prolonged energy generation, resulting in the higher yield. This result shows that the lysate does not contain adverse factors that produce a greater inhibition at such large abundance.

Expression of Target Proteins in a Cell-Free System without an Artificial Energy Regeneration System and in Wheat Germ Extract.

To verify that the cell free expression system without artificial energy regeneration could is generally effective across substrates, the system was used to express 10 additional target gene products other than eYFP. Strep-tagged eYFP and the other 10 target proteins were expressed in 60% BY-2 cell lysate prepared with sorbitol, 40% BY-2 cell lysate prepared with mannitol, and a WGE system from CellFree™ Sciences. Coupled transcription-translation reactions were carried out in 50 μL volume at 25° C. and 700 rpm for 40 hours. Uncoupled transcription and translation reactions using the WGE system were carried out according to the manufacturer's instructions. In each case, 1 μL reaction mix and the mixed bilayer reaction, respectively, was loaded on a 4-12% (w/v) gradient SDS PAGE gel and target proteins were visualized by Coomassie staining. The BYL system successfully transcribed every one of the different genes tested, and also followed the transcription with translation to produce protein in every instance. In fact, the BYL system consistently produced stronger bands, compared to what was produced using the WGE system. For Strep-eYFP, the protein produced in the three systems was quantified using a fluorescence reader and compared to an eYFP standard curve, revealing that 1115 μg/mL and 441 μg/mL were produced under two sets of conditions in the BYL system, and only 105 μg/mL was produced in the WGE system.

Addition of Glucosylglycerol and Use of Higher Lysate Quantities.

To increase the stability of the cell free lysates without artificial energy regeneration, we hypothesized that small molecules described as cryoprotectants for cells and/or proteins may be able to maintain the translational activity of the lysate. Such molecules occur naturally in extremophile organisms, and they protect the extremophiles against osmotic stress, heat, desiccation, and UV light; they stabilize membranes and proteins by causing an increased water density at the surface promoting the protein's natural conformation. It was expected, however, cryoprotectants could exhibit a strong inhibitory effect on the IVTT system.

Different concentrations of the cryoprotectants, ectoine, hydroxyectoine, and glucosylglycerol, were added to coupled IVTT reactions, and the amount of eYFP produced from template plasmid pIVEX_GAAAGA_Omega_Strep-eYFP was determined. 50 μL IVTT reactions (with 60% (v/v) of BYL) were carried out in 96-well plates at 25° C. and 500 rpm for 44 hours, at controlled humidity in a Kuhner shaker™.

Figure 6:
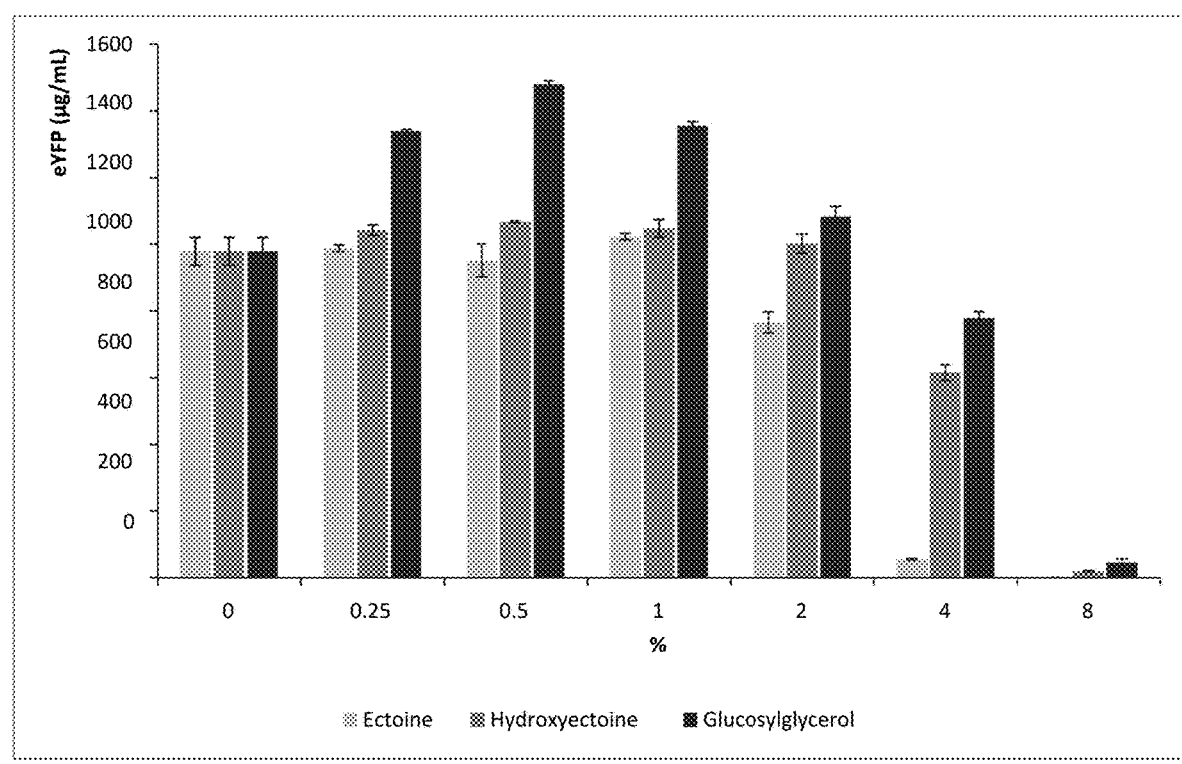
FIG. 6 includes a bar graph showing the effect of ectoine, hydroxyectoine, and glucosylglycerol on eYFP production in a coupled IVTT reaction without artificial energy regeneration. Ectoine, hydroxyectoine, and glucosylglycerol in amounts of 0-8% (v/v) were added to the samples, and plasmid pIVX_GAAAGA_Omega_Strep-eYFP was used as the template. Reactions were carried out using 96-well plates in 50 µL with 60% (v/v) lysate portions, at 25° C. and 500 rpm for 44 hours under controlled humidity (70%). The amount of produced eYFP was determined by use of a fluorescent reader, as compared to an eYFP standard. The eYFP standard was produced using the IVTT transcription-translation system and purified by Strep-Tactin® Sepharose®. The concentration of the purified eYFP was then determined using a colorimetric assay. Data represent the averages and standard deviations of three independent transcription-translation experiments.

Ectoine and hydroxyectoine had no impact on the eYFP yield at concentrations of up to 1% and 2% (v/v), respectively. FIG. 6. In fact, higher concentrations of ectoine and hydroxyectoine inhibited the system. In contrast, glucosylglycerol had a strong positive impact on the eYFP yield. Reactions containing 0.5% (v/v) glucosylglycerol yielded around 50% more eYFP after 44 hour, as compared to standard reactions without glucosylglycerol. FIG. 6.

Figure 7:
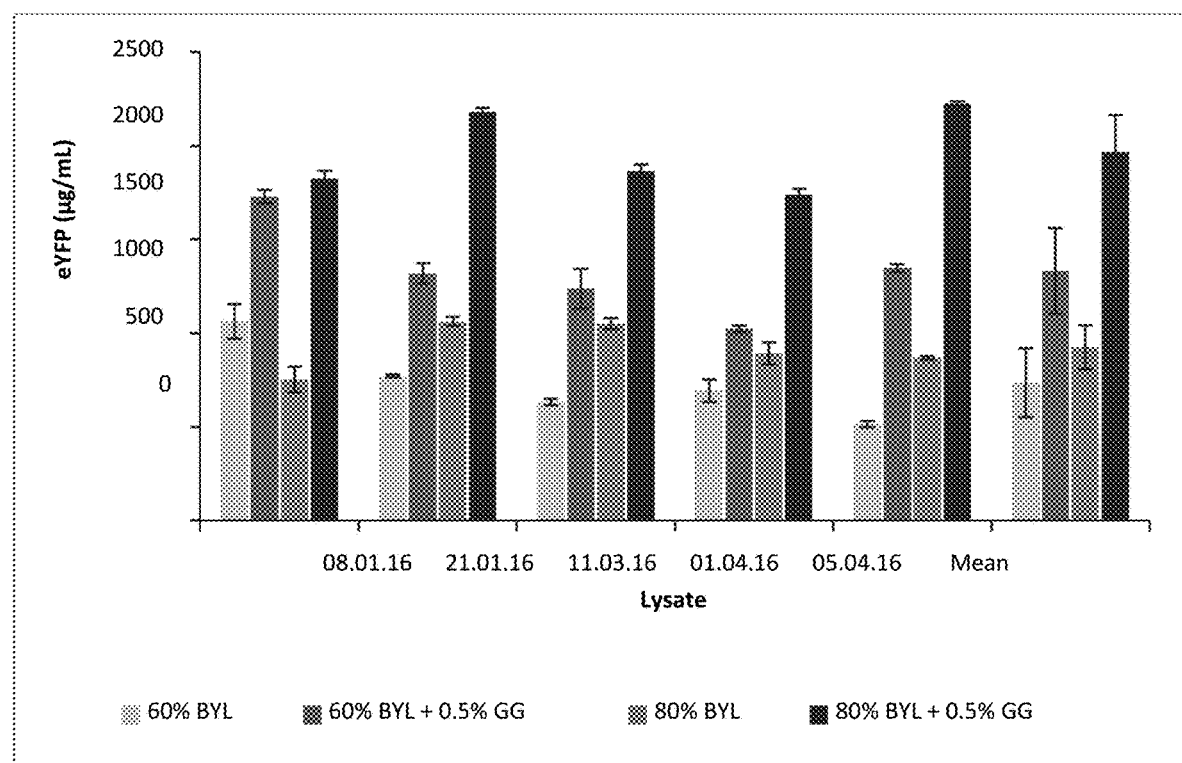
FIG. 7 includes a bar graph showing the impact of glucosylglycerol on coupled IVTT reactions without artificial energy regeneration. The amounts of eYFP produced from plasmid pIVX_GAAAGA_Omega_Strep-eYFP in five different lysate batches were compared. Reactions were carried out with 60% or 80% (v/v) lysate, and without or with 0.5% (v/v) glucosylglycerol (GG). Reactions were in a 50 µL volume in 96-well plates at 25° C. and 500 rpm for 48 hours under controlled humidity (70%). Data represent the averages and standard deviations of three independent transcription-translation experiments.

The positive impact of the glucosylglycerol was consistent across five different lysate batches (BYL 08.01.2016, BYL 21.01.2016, BYL 11.03.2016, BYL 01.04.2016, BYL 05.04.2016) in IVTT reactions without and with 0.5% (v/v) glucosylglycerol. 50 μL IVTT reactions were performed in triplicate with lysate portions of 60% and 80% (v/v) using plasmid pIVEX_GAAAGA_Omega_Strep-eYFP as template in 96-well plates at 25° C. and 500 rpm for 48 hours under controlled humidity (70%). In reactions using 60% (v/v) lysate and 0.5% (v/v) glucosylglycerol, around 80% more eYFP was produced, as compared to reactions without glucosylglycerol. FIG. 7. Using 80% (v/v) lysate and 0.5% (v/v) glucosylglycerol, the eYFP yield increased by about 110% (almost 2 mg/mL eYFP), as compared to reactions using 80% (v/v) lysate without glucosylglycerol. FIG. 7.

Figure 8:
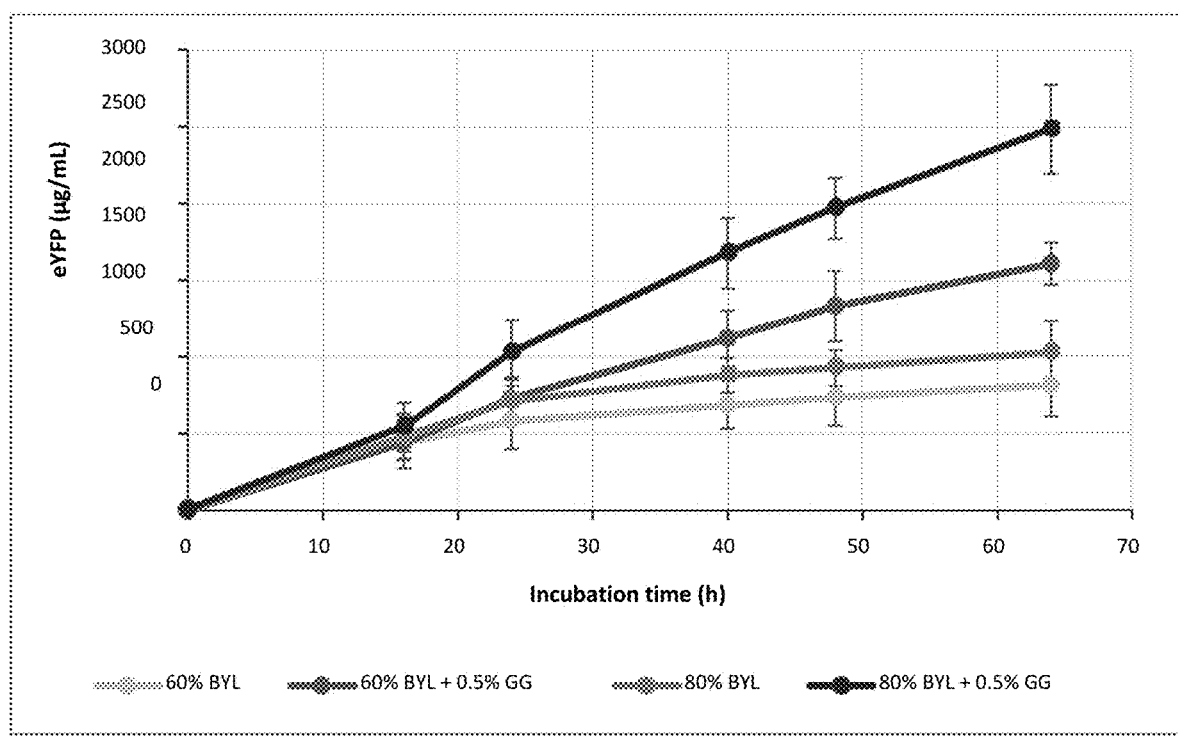
FIG. 8 includes a graphical representation of the time course of eYFP production in coupled IVTT reactions without artificial energy regeneration. Reactions included either 60% or 80% (v/v) lysate, without or with 0.5% (v/v) glucosylglycerol (GG). Plasmid pIVX_GAAAGA_Omega_Strep-eYFP was utilized as the template, and the amount of eYFP produced (as compared to an eYFP standard) was determined by use of a fluorescent reader. Reactions were carried out in 96-well plates with 50 µL volume at 25° C. and 500 rpm for 64 hours under controlled humidity (70%) in a Kuhner™ shaker. Data represent averages and standard deviations of three independent transcription-translation experiments using different lysate batches.

The time course of the IVTT reactions in a cell free system without artificial energy regeneration was determined by measuring the amount of protein produced at different time points, up to 64 hours. FIG. 8. After 16 hours, reactions using 60% or 80% lysate with or without 0.5% glucosylglycerol had produced approximately the same amount of protein. FIG. 8. Without glucosylglycerol, the translational activity in both 60% and 80% (v/v) lysate did not increase further after 24 hours. FIG. 8. However, the eYFP production with glucosylglycerol showed an almost linear increase of productivity until at least 64 hours, in both 60% and 80% (v/v) lysate. FIG. 8. This result confirms that glucosylglycerol has a stabilizing effect on the system that extends the translational activity to beyond 64 hours. On average, the reactions with 80% (v/v) lysate and 0.5% (v/v) glucosylglycerol yielded almost 2.5 mg/mL eYFP.

Addition of Branched Chain Amino Acids.

Figure 9:
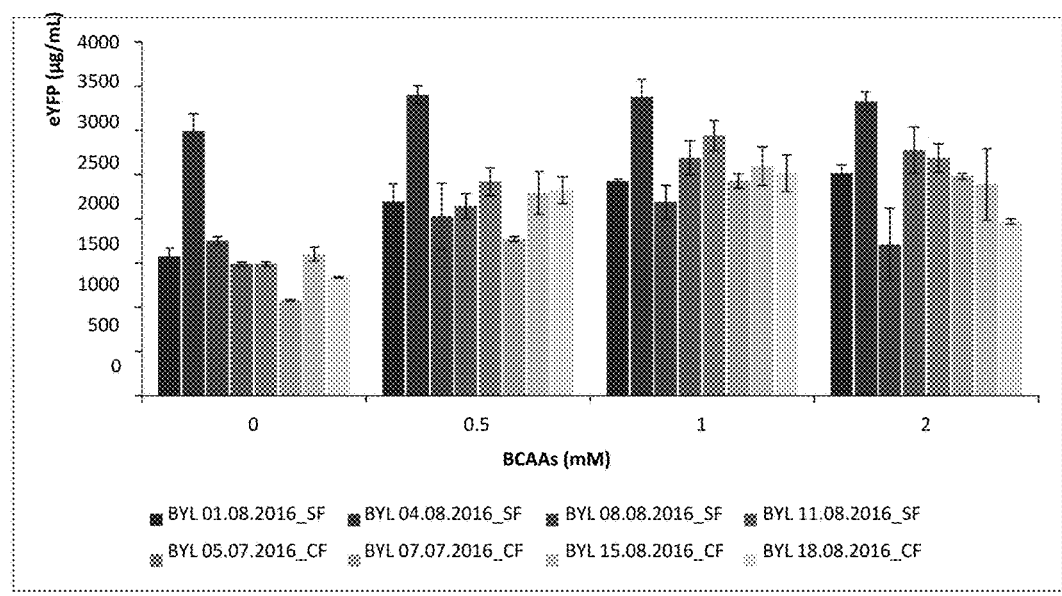
FIG. 9 includes the effect of branched chain amino acids (BCAAs) on eYFP production in coupled IVTT reactions without artificial energy regeneration. 0-2 mM BCAAs were added as the last component to coupled IVTT reactions using plasmid pIVEX_GAAAGA_Omega_Strep-eYFP as template. Reactions were carried out in 96-well plates with 50 µL volume at 25° C. and 500 rpm for 66 hours. The amount of produced eYFP was determined by use of a fluorescent reader, as compared to an eYFP standard. Data represent the averages and standard deviations of six independent transcription-translation experiments. Lysates were prepared from shake flasks (SF) or continuous fermentations (CF).

The ability of branched chain amino acids (BCAAs) to promote protein synthesis in a cell free expression system was also tested, and it was observed that addition of BCAAs increased and stabilized target protein yield. To verify the positive effect of the BCAAs on the system, different concentrations of BCAAs were added to coupled IVTT reactions using four lysates prepared from shake flask (SF) or continuous fermentation (CF). In 50 μL IVTT reactions with 80% (v/v) lysate in 96-well plates at 25° C. and 500 rpm for 66 hours using plasmid template pIVEX_GAAAGA_Omega_Strep-eYFP at controlled humidity in the Kuhner™ shaker, the BCAAs had a positive impact on the eYFP yield at all tested concentrations, no matter whether the lysates were prepared from shake flask or continuous fermentation. FIG. 9. Reactions containing 1 mM BCAAs yielded around 70% more eYFP (average yield of 2.5 mg eYFP per mL), as compared to reactions without BCAAs.

The invention claimed is:

1. A system for synthesis of a polypeptide, the system comprising a reaction volume comprising:
   an aqueous cellular lysate from tobacco plants that comprises mitochondria;
   an exogenous nucleic acid template encoding a polypeptide; and
   nucleotide triphosphates (NTPs),
   wherein the system does not comprise creatine phosphate and creatine kinase that are exogenous to the cellular lysate and mitochondria.

2. The system of claim 1, wherein the reaction volume further comprises exogenous RNA polymerase.

3. The system of claim 2, wherein the reaction volume is buffered to pH 7.8.

4. The system of claim 1, wherein the reaction volume further comprises chloramphenicol.

5. The system of claim 1, wherein the cellular lysate from tobacco plant cells is evacuolated.

6. The system of claim 5, wherein the cellular lysate from tobacco plant cells that comprises mitochondria has been treated with a ribonuclease to destroy endogenous ribonucleic acids.

7. The system of claim 6, wherein the exogenous nucleic acid template is deoxyribonucleic acid (DNA).

8. The system of claim 7, wherein the exogenous nucleic acid template is comprised by a vector.

9. The system of claim 6, wherein the reaction volume consists essentially of:
   an evacuolated cellular lysate from tobacco plants that comprises mitochondria and that has been treated to destroy endogenous ribonucleic acids;
   a vector comprising the exogenous nucleic acid template that is a vector molecule;
   HEPES-KOH, pH 7.8;
   $Mg(C_5H_8NO_4)_2$;
   $KC_5H_8NO_4$;
   nucleotide triphosphates;
   RNA polymerase; and
   chloramphenicol.

10. The system of claim 1, wherein the reaction volume comprises less than 15 mM creatine phosphate.

11. The system of claim 1, wherein the reaction volume comprises less than 10 mM creatine phosphate.

12. A method for synthesizing a polypeptide, the method comprising:
    adding the exogenous nucleic acid template encoding a polypeptide to the aqueous cellular lysate from tobacco plants that comprises mitochondria and the NTPs in the system of claim 1.

13. The method according to claim 12, the method further comprising isolating the polypeptide encoded by the nucleic acid template.

14. A kit for synthesizing a polypeptide, the kit comprising: an evacuolated aqueous cellular lysate from tobacco plant cells that comprises mitochondria that is treated to destroy endogenous ribonucleic acids (RNAs);
    nucleotide triphosphates (NTPs), wherein the NTPs and the aqueous cellular lysate are disposed in one or more separate volumes from the cellular lysate from tobacco plant cells that comprises mitochondria; and
    instructions directing a user to combine the cellular lysate from tobacco plant cells that comprises mitochondria, the NTPs, and an exogenous nucleic acid template encoding the polypeptide in a reaction volume,
    wherein the kit does not comprise creatine phosphate and creatine kinase that are exogenous to the cellular lysate and mitochondria.

15. The kit of claim 14, wherein the cellular lysate comprising mitochondria and NTPs are disposed in one volume.

16. The kit of claim 14, wherein the instructions direct the user to combine the evacuolated cellular lysate, the NTPs, and the exogenous nucleic acid template encoding the polypeptide in the reaction volume without adding creatine phosphate.

17. The kit of claim 14, further comprising at least one vector suitable for expressing the exogenous nucleic acid template in the evacuolated cellular lysate.

18. A method for synthesizing a polypeptide with the kit of claim 14, the method comprising:
    combining the evacuolated cellular lysate from tobacco plant cells that comprises mitochondria, the NTPs, and an exogenous nucleic acid template encoding a polypeptide in a reaction volume.

* * * * *

SEQUENCE LISTING

```
<160> NUMBER OF SEQ ID NOS: 24

<210> SEQ ID NO 1
<211> LENGTH: 93
<212> TYPE: DNA
<213> ORGANISM: Artificial Sequence
<220> FEATURE:
<223> OTHER INFORMATION: Primer

<400> SEQUENCE: 1
taatacgact cactatagaa agagtatttt tacaacaatt accaacaaca acaacaaaca      60
acaacaacat tacattttac attctacaac tac                                  93

<210> SEQ ID NO 2
<211> LENGTH: 101
<212> TYPE: DNA
<213> ORGANISM: Artificial Sequence
<220> FEATURE:
<223> OTHER INFORMATION: Primer

<400> SEQUENCE: 2
catggtagtt gtagaatgta aaatgtaatg ttgttgttgt tgttgttgt tgttggtaat       60 tgttgtaaaa atactctttc tatagtgagt cgtattacat g                        101

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
gatcatacat gtggtctcat ccgcaattc                                       29

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
gatcatggta ccttattact tgtacagctc gtcc                                 34
```

```
<210> SEQ ID NO 5
<211> LENGTH: 62
<212> TYPE: DNA
<213> ORGANISM: Artificial Sequence
<220> FEATURE:
<223> OTHER INFORMATION: Primer

<400> SEQUENCE: 5
caacaacatt acattttaca ttctacaact acatgaatca aaataaacac ggaattattg    60
gc                                                                  62

<210> SEQ ID NO 6
<211> LENGTH: 60
<212> TYPE: DNA
<213> ORGANISM: Artificial Sequence
<220> FEATURE:
<223> OTHER INFORMATION: Primer

<400> SEQUENCE: 6
gtccaaacca aaccagaaga gctgggtacc ctattacttt tctgtttcaa cgaattcaat    60

<210> SEQ ID NO 7
<211> LENGTH: 64
<212> TYPE: DNA
<213> ORGANISM: Artificial Sequence
<220> FEATURE:
<223> OTHER INFORMATION: Primer

<400> SEQUENCE: 7
caacaacatt acattttaca ttctacaact acatgaataa tgtattgaat agtggaagaa    60
caac                                                                64

<210> SEQ ID NO 8
<211> LENGTH: 60
<212> TYPE: DNA
<213> ORGANISM: Artificial Sequence
<220> FEATURE:
<223> OTHER INFORMATION: Primer

<400> SEQUENCE: 8
gtccaaacca aaccagaaga gctgggtacc ctattaataa agtggtgaaa tattagttgg    60

<210> SEQ ID NO 9
<211> LENGTH: 60
<212> TYPE: DNA
<213> ORGANISM: Artificial Sequence
<220> FEATURE:
<223> OTHER INFORMATION: Primer

<400> SEQUENCE: 9
caacaacatt acattttaca ttctacaact acatggctca gaccactctc caaatcacac    60

<210> SEQ ID NO 10
<211> LENGTH: 58
<212> TYPE: DNA
<213> ORGANISM: Artificial Sequence
<220> FEATURE:
<223> OTHER INFORMATION: Primer

<400> SEQUENCE: 10
gtccaaacca aaccagaaga gctgggtacc ttatcaaacc aaggcagcac cctcagtt      58

<210> SEQ ID NO 11
<211> LENGTH: 58
<212> TYPE: DNA
```

```
<213> ORGANISM: Artificial Sequence
<220> FEATURE:
<223> OTHER INFORMATION: Primer

<400> SEQUENCE: 11
caacaacatt acattttaca ttctacaact acatgaacaa tgtgctgaac tctggtcg        58

<210> SEQ ID NO 12
<211> LENGTH: 58
<212> TYPE: DNA
<213> ORGANISM: Artificial Sequence
<220> FEATURE:
<223> OTHER INFORMATION: Primer

<400> SEQUENCE: 12
gtccaaacca aaccagaaga gctgggtacc ctatcagtag aggggaggaa ggttggtc        58

<210> SEQ ID NO 13
<211> LENGTH: 61
<212> TYPE: DNA
<213> ORGANISM: Artificial Sequence
<220> FEATURE:
<223> OTHER INFORMATION: Primer

<400> SEQUENCE: 13
caacaacatt acattttaca ttctacaact acatgaatcc gaacaatcga agtgaacatg      60
a                                                                      61

<210> SEQ ID NO 14
<211> LENGTH: 60
<212> TYPE: DNA
<213> ORGANISM: Artificial Sequence
<220> FEATURE:
<223> OTHER INFORMATION: Primer

<400> SEQUENCE: 14
tccaaaccaa accagaagag ctgggtacct cattaattca ctggaataaa ttcaattttg      60

<210> SEQ ID NO 15
<211> LENGTH: 56
<212> TYPE: DNA
<213> ORGANISM: Artificial Sequence
<220> FEATURE:
<223> OTHER INFORMATION: Primer

<400> SEQUENCE: 15
caacaacatt acattttaca ttctacaact acatggccca gtctagccgc atctgc          56

<210> SEQ ID NO 16
<211> LENGTH: 60
<212> TYPE: DNA
<213> ORGANISM: Artificial Sequence
<220> FEATURE:
<223> OTHER INFORMATION: Primer

<400> SEQUENCE: 16
tccaaaccaa accagaagag ctgggtaccc tatcacttga tcgagaaatc gcgaaagttg      60

<210> SEQ ID NO 17
<211> LENGTH: 65
<212> TYPE: DNA
<213> ORGANISM: Artificial Sequence
<220> FEATURE:
<223> OTHER INFORMATION: Primer

<400> SEQUENCE: 17
```

```
caacaacatt acattttaca ttctacaact acatgaatat gaataatact aaattaaacg    60
caagg                                                                65

<210> SEQ ID NO 18
<211> LENGTH: 60
<212> TYPE: DNA
<213> ORGANISM: Artificial Sequence
<220> FEATURE:
<223> OTHER INFORMATION: Primer

<400> SEQUENCE: 18
gtccaaacca aaccagaaga gctgggtacc tcattactta attgaaaaat ctcggaaatt    60

<210> SEQ ID NO 19
<211> LENGTH: 66
<212> TYPE: DNA
<213> ORGANISM: Artificial Sequence
<220> FEATURE:
<223> OTHER INFORMATION: Primer

<400> SEQUENCE: 19
caacaacatt acattttaca ttctacaact acatgattat tgatagtaaa acgactttac    60
ctagac                                                               66

<210> SEQ ID NO 20
<211> LENGTH: 60
<212> TYPE: DNA
<213> ORGANISM: Artificial Sequence
<220> FEATURE:
<223> OTHER INFORMATION: Primer

<400> SEQUENCE: 20
tccaaaccaa accagaagag ctgggtacct cattaattat tataccaatc cgaattatta    60

<210> SEQ ID NO 21
<211> LENGTH: 60
<212> TYPE: DNA
<213> ORGANISM: Artificial Sequence
<220> FEATURE:
<223> OTHER INFORMATION: Primer

<400> SEQUENCE: 21
caacaacatt acattttaca ttctacaact acatgtacac aagtatttat aaattagagg    60

<210> SEQ ID NO 22
<211> LENGTH: 60
<212> TYPE: DNA
<213> ORGANISM: Artificial Sequence
<220> FEATURE:
<223> OTHER INFORMATION: Primer

<400> SEQUENCE: 22
gtccaaacca aaccagaaga gctgggtacc ctattactct tttttgtcat tatgttgatt    60

<210> SEQ ID NO 23
<211> LENGTH: 63
<212> TYPE: DNA
<213> ORGANISM: Artificial Sequence
<220> FEATURE:
<223> OTHER INFORMATION: Primer

<400> SEQUENCE: 23
caacaacatt acattttaca ttctacaact acatggaaaa taatattcaa aatcaatgcg    60
```

```
tac                                                              63

<210> SEQ ID NO 24
<211> LENGTH: 60
<212> TYPE: DNA
<213> ORGANISM: Artificial Sequence
<220> FEATURE:
<223> OTHER INFORMATION: Primer

<400> SEQUENCE: 24
gtccaaacca aaccagaaga gctgggtacc ctattattcc tccataagaa gtaattccac    60
```